(12) United States Patent
McCombs

(10) Patent No.: US 8,597,316 B2
(45) Date of Patent: Dec. 3, 2013

(54) CUTTING ACCESSORY FOR USE WITH A MEDICAL/SURGICAL POWERED HANDPIECE, THE ACCESSORY HAVING RETENTION FEATURES THAT FACILITATE THE FINE OR COARSE ADJUSTMENT OF THE EXTENSION OF THE ACCESSORY SHAFT

(75) Inventor: Daniel L. McCombs, Paw Paw, MI (US)

(73) Assignee: Stryker Corporation, Kalamazoo, MI (US)

( * ) Notice: Subject to any disclaimer, the term of this patent is extended or adjusted under 35 U.S.C. 154(b) by 1387 days.

(21) Appl. No.: 12/205,103

(22) Filed: Sep. 5, 2008

(65) Prior Publication Data

US 2010/0063524 A1    Mar. 11, 2010

(51) Int. Cl.
*A61B 17/32* (2006.01)
(52) U.S. Cl.
USPC .................. 606/167; 606/170; 606/169
(58) Field of Classification Search
USPC .......................................... 606/167, 170, 169
See application file for complete search history.

(56) References Cited

U.S. PATENT DOCUMENTS

| | | | |
|---|---|---|---|
| 4,873,461 A | 10/1989 | Brennan et al. | |
| 5,741,263 A | 4/1998 | Umber et al. | |
| 5,888,200 A | 3/1999 | Walen | |
| 6,562,055 B2 | 5/2003 | Walen | |
| 2002/0058958 A1* | 5/2002 | Walen | 606/170 |
| 2002/0151902 A1 | 10/2002 | Riedel | |
| 2003/0060829 A1 | 3/2003 | Del Rio et al. | |
| 2005/0072007 A1 | 4/2005 | Proulx | |
| 2005/0116578 A1 | 6/2005 | Fleury | |
| 2006/0053974 A1 | 3/2006 | Blust et al. | |
| 2007/0119055 A1 | 5/2007 | Walen et al. | |

FOREIGN PATENT DOCUMENTS

| | | |
|---|---|---|
| CN | 100442967 | 12/2008 |
| CN | 101299969 B | 4/2011 |

OTHER PUBLICATIONS

European Patent Office, "International Search Report and Written Opinion for PCT App. No. PCT/US2009/055670", Sep. 29, 2010.
Chinese Patent Office, "Office Action", for CN Application No. 2009801442482, Feb. 2013.

* cited by examiner

*Primary Examiner* — Cherie M Stanfield

(57) ABSTRACT

A surgical tool system including a handpiece with a motor and a cutting accessory with a shaft that is rotated by the handpiece motor. The handpiece includes a coupling assembly with plural locking elements for holding the accessory shaft to an output drive shaft that is actuated by the handpiece motor. The locking elements are longitudinally spaced apart from each other. The accessory shaft is formed with retention features against which the handpiece locking elements engage. The shaft retention features are in columns. The retention features in adjacent retention features are longitudinally offset from each other. This allows the coarse or fine adjustment of the extent to which the accessory shaft extends forward from the handpiece coupling assembly.

23 Claims, 18 Drawing Sheets

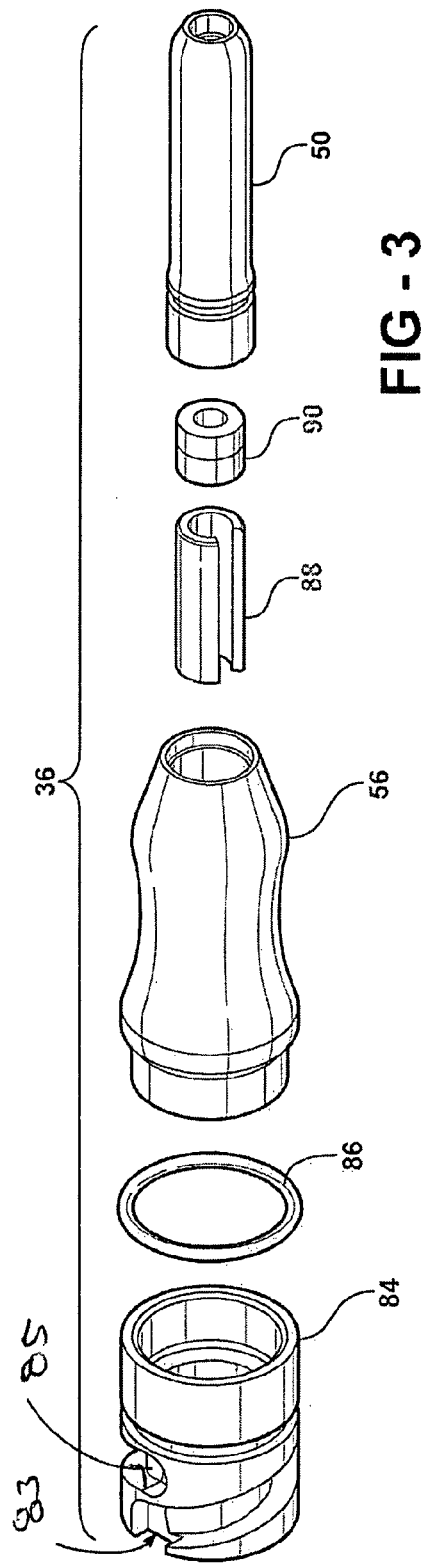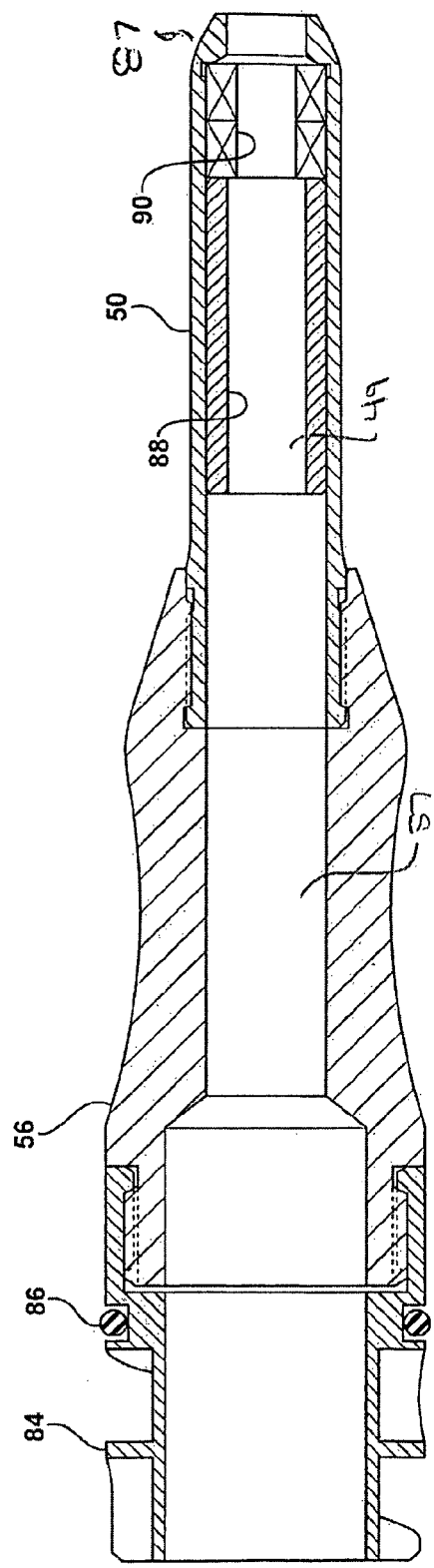

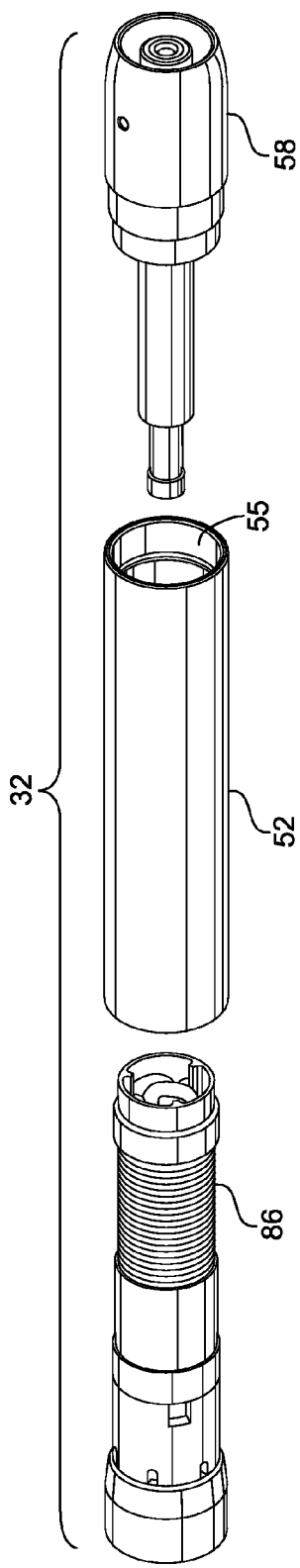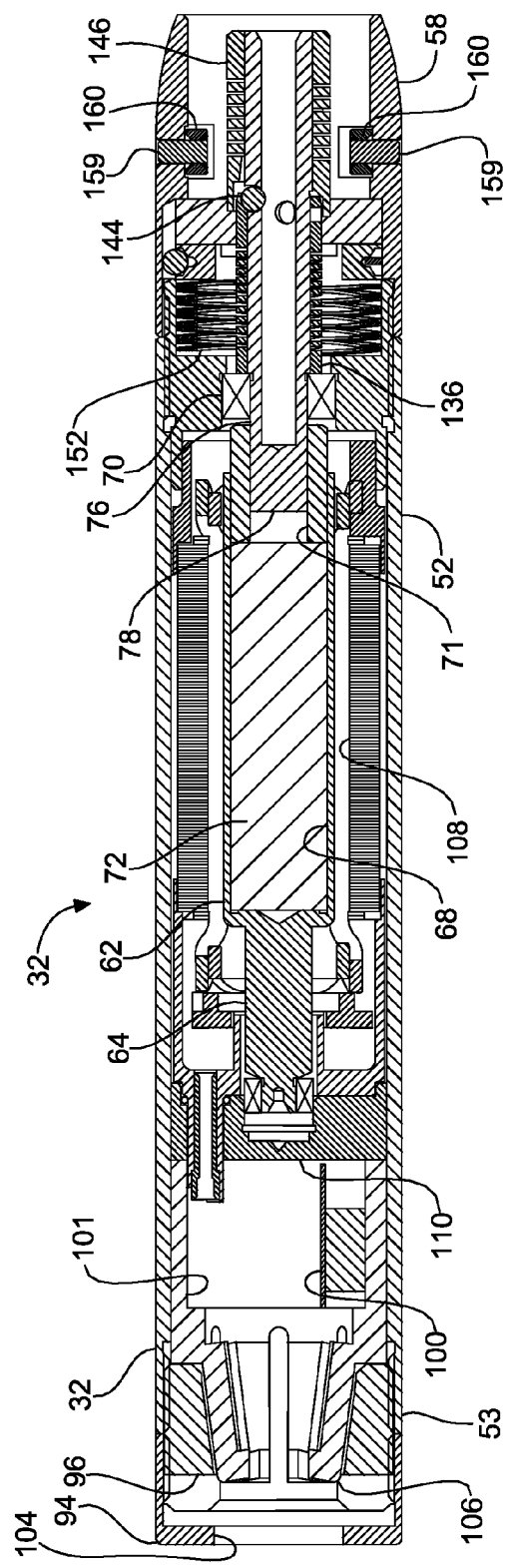

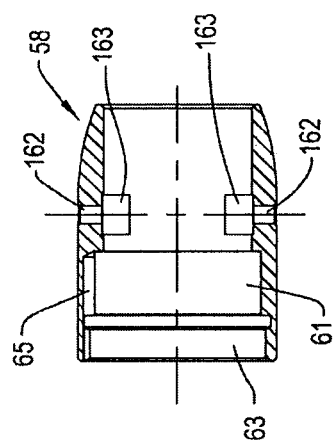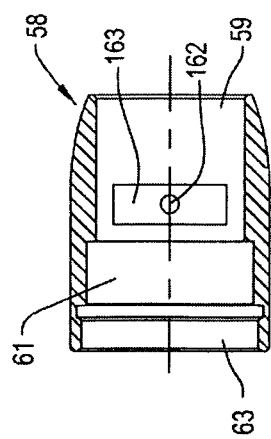

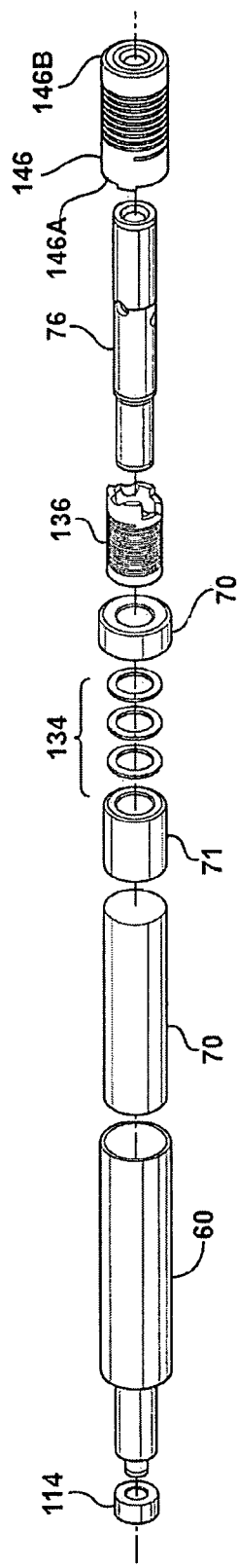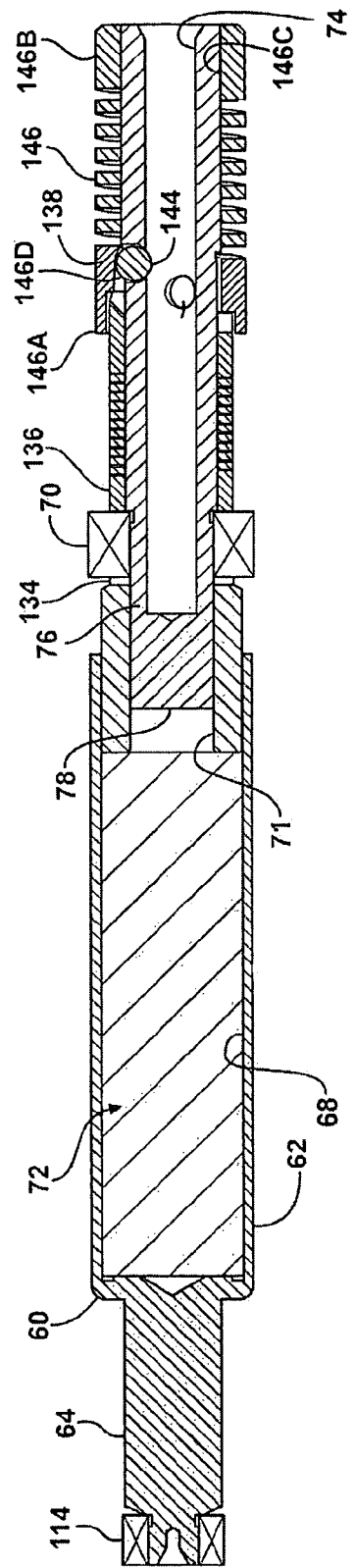

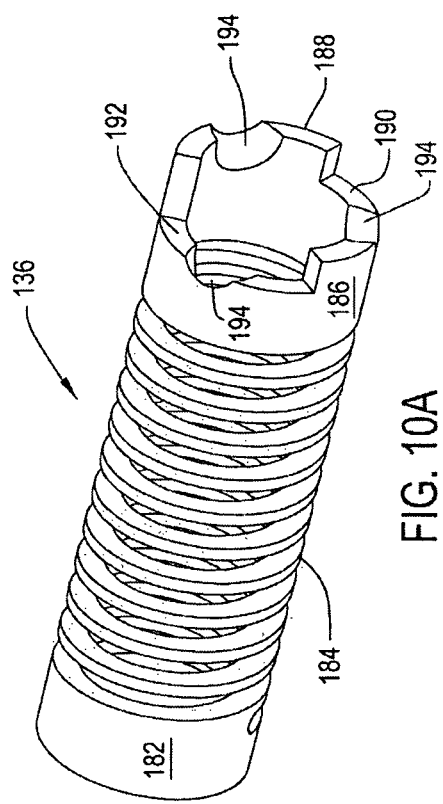
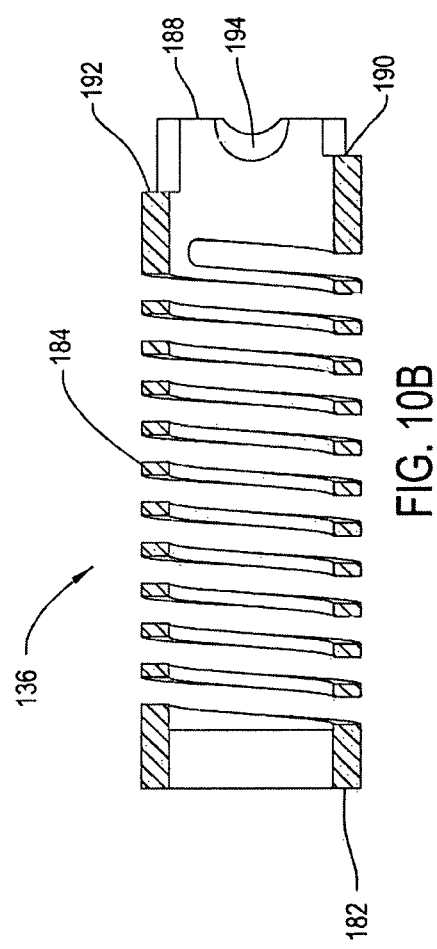
FIG. 10A
FIG. 10B

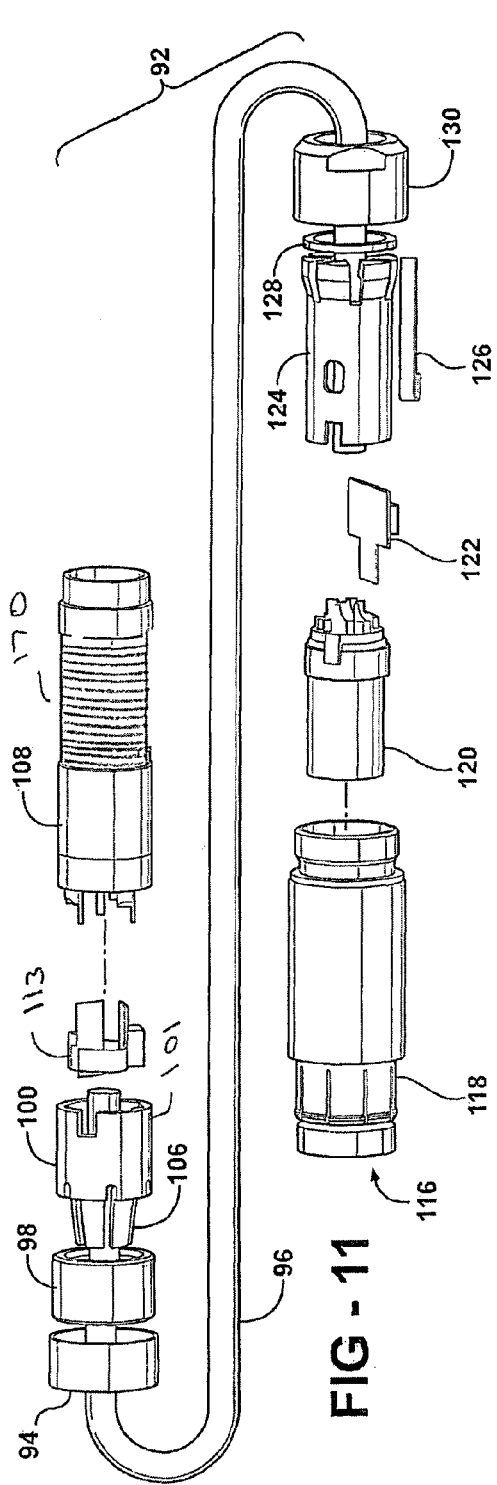
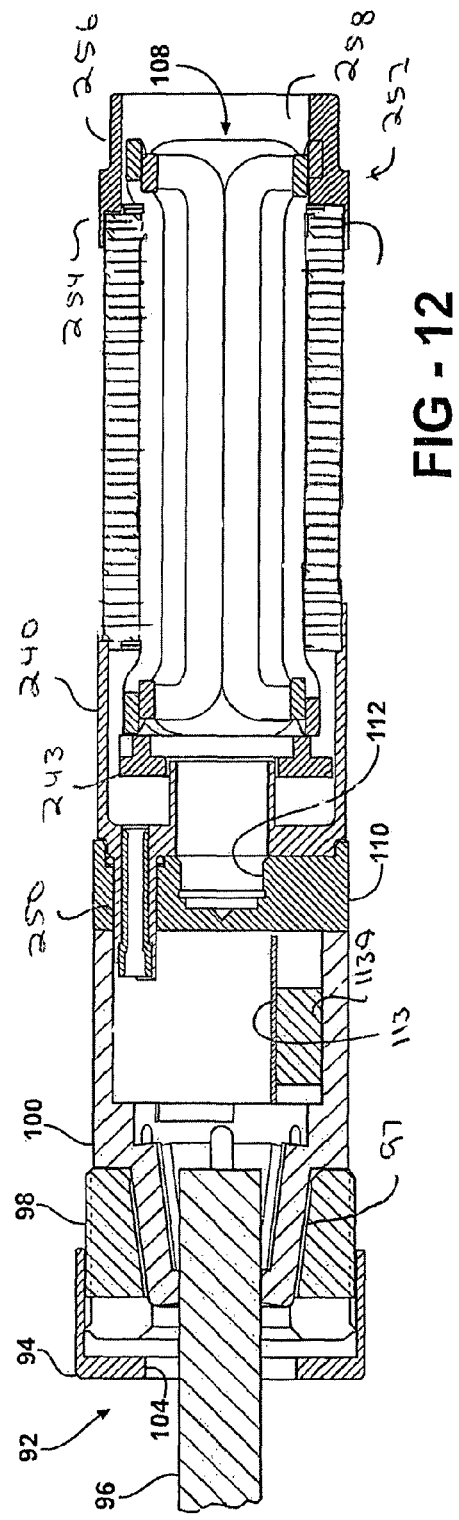

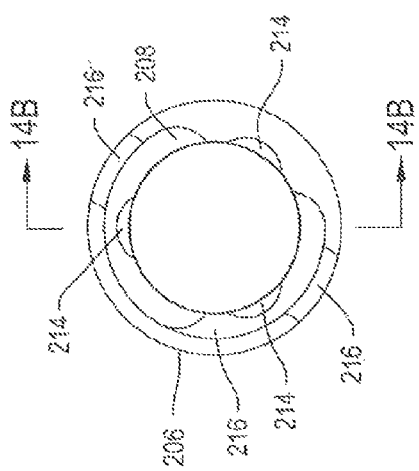
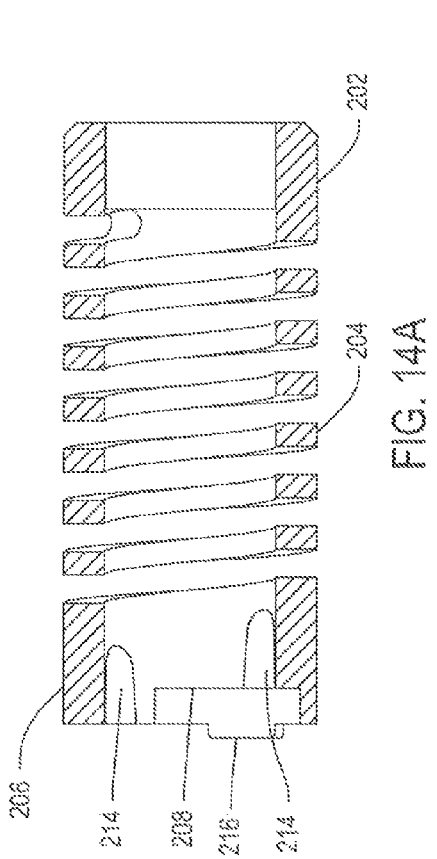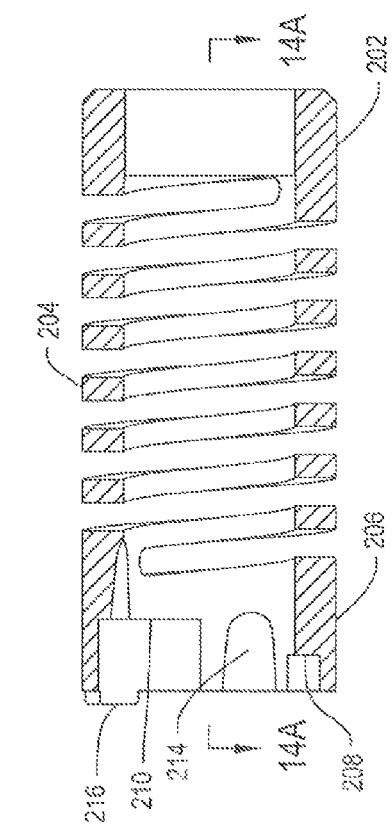

CUTTING ACCESSORY FOR USE WITH A MEDICAL/SURGICAL POWERED HANDPIECE, THE ACCESSORY HAVING RETENTION FEATURES THAT FACILITATE THE FINE OR COARSE ADJUSTMENT OF THE EXTENSION OF THE ACCESSORY SHAFT

FIELD OF THE INVENTION

The present invention relates generally to a surgical tool system to which accessories are selectively attached. More particularly, this invention relates to a surgical tool system and a complementary accessory that are collectively configured to allow the longitudinal position of the accessory relative the handpiece to be selectively finely or coarsely set.

BACKGROUND OF THE INVENTION

In modern surgery, one of the most important instruments available to medical personnel is the powered surgical tool. Typically, this tool comprises some type of handpiece in which a motor is housed. Secured to the handpiece is an accessory designed for application to a surgical site on a patient in order to accomplish a specific medical task. Some powered surgical tools are provided with drills or burs for cutting bores into hard tissue or for selectively removing the hard tissue. Still other powered surgical tools are provided with saw blades as cutting accessories. These tools are used for separating large sections of hard and/or soft tissue. The ability to use powered surgical tools on a patient has lessened the physical strain of physicians and other medical personnel when performing procedures on a patient. Moreover, most surgical procedures can be performed more quickly, and more accurately, with powered surgical tools than with the manual equivalents that preceded them.

The Applicant's Assignee's U.S. Pat. No. 5,888,200, entitled, MULTI-PURPOSE SURGICAL TOOL SYSTEM, issued Mar. 30, 1999, incorporated herein by reference, discloses a surgical tool system designed for a number of different applications. This tool system includes a handpiece in which a motor is housed. The handpiece also includes a first coupling assembly for selectively coupling the shaft of an accessory to the motor shaft. This handpiece also includes a second coupling assembly. The second coupling assembly is used to selectively secure an attachment to the front end of the handpiece. This attachment may include its own drive shaft and accessory coupling assembly. These attachments are elongated attachments, angled attachments and/or able to actuate saw blades. Thus, an advantage of providing this type of tool system is that a single handpiece can be used to drive a large number of different cutting accessories and facilitate the positioning of the accessories at the surgical site in a manner that is either required or desired for a particular surgical procedure.

Popular cutting accessories that are used with this type of surgical tool system include drills and burs. Each of these cutting accessories typically has a head that forms the actual tissue removal member of the accessory. A shaft extends rearwardly from the head. The shaft is the component of the cutting accessory against which the coupling assembly locks.

There is a limitation associated with the above-described system. The coupling assembly of this system is designed so that a cutting accessory can only be secured to it in a single, fixed location relative to the handpiece. A disadvantage of this arrangement is that surgeons frequently find it useful to have some degree of flexibility in positioning the head of the cutting accessory relative to the handpiece. To date, to offer this flexibility, it is necessary to provide a set of cutting accessories that have identical cutting heads. The difference between the accessories is the length of their complementary shafts. When a surgeon wants the head of the accessory to be positioned relatively close to the handpiece, he/she installs in the handpiece a cutting accessory with a shaft that is relatively short in length. If the surgeon wants the head of the accessory to be spaced a distance from the handpiece, he/she installs in the handpiece a cutting accessory that has a relatively long shaft.

Moreover, during a surgical procedure, a surgeon may want to use different tools to access different locations at the surgical site. Alternatively, surgeons have individual preferences regarding how they want to view a surgical site and/or handle their surgical tools. In order to accommodate these variations, surgical tool systems are provided with members that vary in only the geometry and/or dimensions of the components employed to transfer the power developed by the handpiece motor to the associated cutting accessory. For example, the tool system described in the above-referenced U.S. Pat. No. 5,888,200 has different length attachments and attachments that have distal end sections that are straight and angled from the associated handpiece housing. If surgeon has to access a surgical site located close to the skin of the patient he/she has available a medium length attachment. Alternatively, if the surgeon has to access a surgical site deep within the patient, the surgeon has available a long attachment. This attachment, in comparison to the medium length attachment, holds the head of the cutting accessory a relatively long distance away from handpiece. Angled attachments are also available. These attachments are used to hold the cutting accessory at an angle that is offset to the longitudinal axis of the handpiece. Angled attachments are used to position the cutting accessory at surgical sites that are difficult to reach and/or to provide a surgeon with an alternative field of view of the surgical site.

Clearly, having these different attachments available is beneficial to the surgeon. However, the coupling assemblies internal to these attachments are often located different longitudinal distances from their head ends, theirs distal ends, the ends from which the shaft of the accessory emerges. In order to use these attachments, it is necessary to provide cutting accessories with the same head but that have different length shafts. Accessories with short length shafts are fitted into attachments in which the coupling assemblies are positioned relatively short distances from their distal end openings. Accessories with long length shafts are fitted into attachments in which the coupling assemblies are positioned longer distances from their distal end openings. This is another reason why it is sometimes necessary to have a number of different cutting accessories available for use in a single surgical procedure that vary only in their shaft length.

Another limitation associated with cutting accessories such as drills and burs is related to the fact that sometimes a number of different accessories are packaged as a set. These accessories are so packaged together because a surgeon, during a procedure, may want to view the complete set of accessories he/she has available for use. Alternatively, prior to the beginning of a surgical procedure, a number of individual accessories are each unpackaged and arranged as a set for the surgeon. Again, this is to allow the surgeon to both view and have easy access to a number of different accessories.

However, often, during a procedure, the surgeon does not use all of the cutting accessories that have been unwrapped from their sterile packaging. The accessories that are used are typically discarded. This is because the cutting heads of these accessories are at least partially worn. However, after the procedure, there may be one or more exposed cutting accessories that were not used. These accessories can be used in a new procedure, if prior to reuse they are sterilized to remove any contaminates they may have picked up as a result of their exposure to the environment. In a procedure used to sterilize these accessories they are heated to a temperature of approximately 132 C., and subjected to saturated water vapor at a pressure of 2.1 bars. These accessories are formed of tool steel because cutting surfaces formed from this material tends to wear at a slower rate cutting surfaces formed from stainless steel. Also, tool steel is less expensive than an alternative material, carbide steel. However, during the above-described sterilization process, the tool steel tends to discolor. This discoloration is disconcerting to medical personnel. Consequently, medical personnel are reluctant to use these unused autoclave-sterilized accessories even though their quality and the degree of sterilization is the same as accessories that have just been removed from the manufacturer's packaging. Thus, there is tendency to discard these unused accessories even though, with proper sterilization, they can be available for use in a later procedure. The discarding of these cutting accessories, even though they have not even been used, is a waste of resources.

The Applicant's Assignee's U.S. Pat. No. 6,562,055 provides a surgical tool system to which cutting accessories are selectively attached. The surgical tool system in the '055 patent includes a specially designed cutting accessory with retention features. As shown in FIGS. 40 and 41 of the '055 patent, the retention features are comprised of cut-outs in the shaft of the cutting accessory. The cutouts work with a locking mechanism which allows the longitudinal position of the accessory relative to a hand tool to be adjusted. The relative position may be adjusted between positions defined by the cutouts and the distance between positions is equal to the longitudinal distance between the cutouts. Thus, in the "055 system, the relative position may only be adjusted in increments equal to this distance. Practically it has been found that the retention features need to be spaced apart a minimum of 2.4 mm. If the retention features are spaced apart smaller distances, the features would therefore be smaller. The complementary coupling features of the handpiece coupling assembly might then not be able to grasp the retention features over a large enough surface area to ensure the transfer of torque from the handpiece coupling features to the accessory shaft.

SUMMARY OF THE INVENTION

This invention is related to a new and useful surgical tool assembly. The tool assembly of this invention includes a handpiece with a motor. The motor may be electric or pneumatic. An output drive shaft is connected to the rotor integral with the motor to rotate with the rotor. A coupling assembly releaseably holds the shaft of a cutting accessory to the output drive shaft so the accessory shaft rotates with the output drive shaft. The coupling assembly includes a number of locking elements. The locking elements are both arcuately spaced apart from each and, along the longitudinal axis of the output drive shaft, spaced apart from each other.

Another aspect of the present invention, is the geometry of the accessory designed for use with the above-described surgical tool. The accessory includes an elongated shaft, a head, and a plurality of retention features. The elongated shaft has a distal end, a proximal end, and a longitudinal axis. The head is connected to the shaft at the distal end. The plurality of retention features are arranged in columns of plural retention features. The columns are arcuately spaced around the accessory shaft. The retention features are further aligned so that retention features in one column are longitudinally offset relative to the retention features in the other columns.

Using the tool system of this invention, one can adjust the distance the accessory shaft extends forward from the coupling assembly by pushing or pulling on the accessory shaft. This motion would cause each locking element to serially engage the retention features in a single column of retention features. This adjustment would result the adjustment of shaft by units equal to the longitudinal separation of the retention features in a single column, a coarse adjustment of shaft extension/retraction. Alternatively, one could adjust accessory shaft extension/retraction by rotating the accessory shaft. This action results in each cutting accessory locking element engaging the retention feature in a first column and then engaging the retention feature in a second adjacent column. The longitudinal spacing between the shaft retention features between features of adjacent columns is less than the spacing between the features in a single column. Accordingly, this resetting of accessory shaft position results in a smaller incremental change, a finer change, in shaft position than in the coarse resetting process.

In a further another aspect of the present invention, a DC brushless motor having a housing, a coil assembly, a rotor, and a pie magnet assembly is provided. The coil assembly is coupled to the housing. The coil assembly has a sleeve and a plurality of windings interlaced about the sleeve. The windings are constructed from wire having a generally rectangular cross-section. The rotor has a bore and is rotatably coupled to the housing. The pie magnet assembly being located within the bore.

BRIEF DESCRIPTION OF THE DRAWINGS

Other advantages of the present invention will be readily appreciated as the same becomes better understood by reference to the following detailed description when considered in connection with the accompanying drawings wherein:

FIG. 3 is an exploded view of the attachment;

FIG. 4 is a cross-section of the attachment of FIG. 3;

FIG. 5 is an exploded view of a handpiece of the tool system of FIG. 1;

FIG. 6 is a cross-section of the handpiece of FIG. 5;

FIG. 8A is a first cross sectional view of the coupling assembly collar;

FIG. 8B is a second cross sectional view of the coupling assembly collar taken along a plane rotated 90° from the plane of the view in which view of FIG. 8A is taken;

FIG. 9 is an exploded view of the motor rotor and a portion of the coupling assembly of the handpiece of this invention;

FIG. 10 is a cross-section of the motor rotor and a portion of the coupling assembly of the handpiece of this invention;

FIG. 10A is a perspective view of the coupling assembly ratchet spring;

FIG. 10B is a cross sectional view of the ratchet spring taken along a plane that includes the longitudinal axis of the spring;

FIG. 11 is an exploded view of a cable assembly of the tool system of FIG. 1;

FIG. 12 is a cross-section view of the cable and motor internal to the handpiece;

FIG. 14A is a first cross-section of a lock spring of the tool system of FIG. 1;

FIG. 14B is a second cross-section of the lock spring of FIG. 14A;

FIG. 14C is a proximal end view of the lock spring of FIG. 14A;

DETAILED DESCRIPTION OF INVENTION

Figure 1:
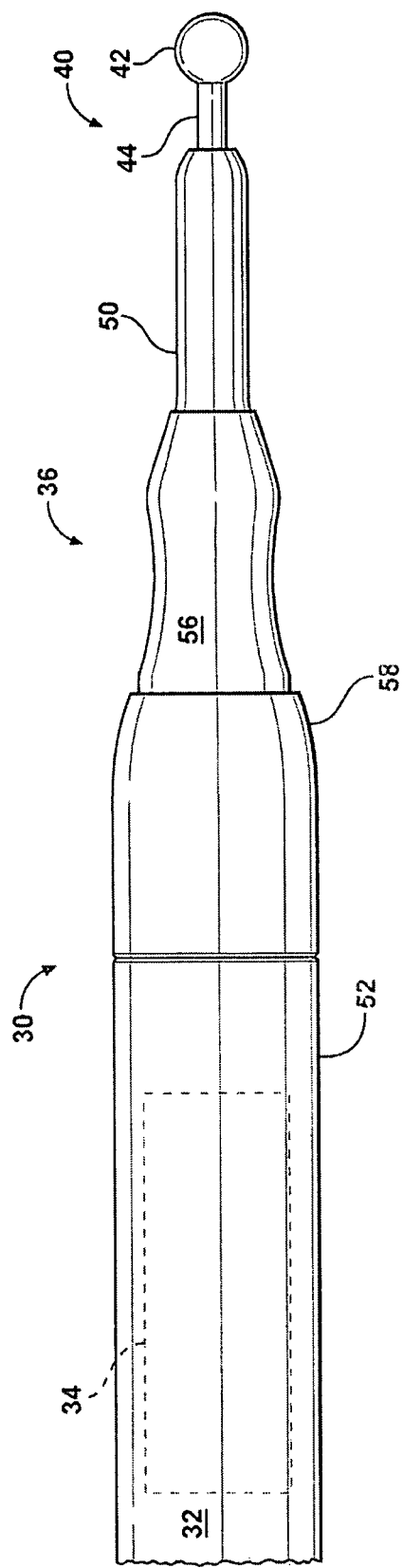
FIG. 1 is plan view of the basic components of the tool system, according to an embodiment of the present invention.
Figure 2:
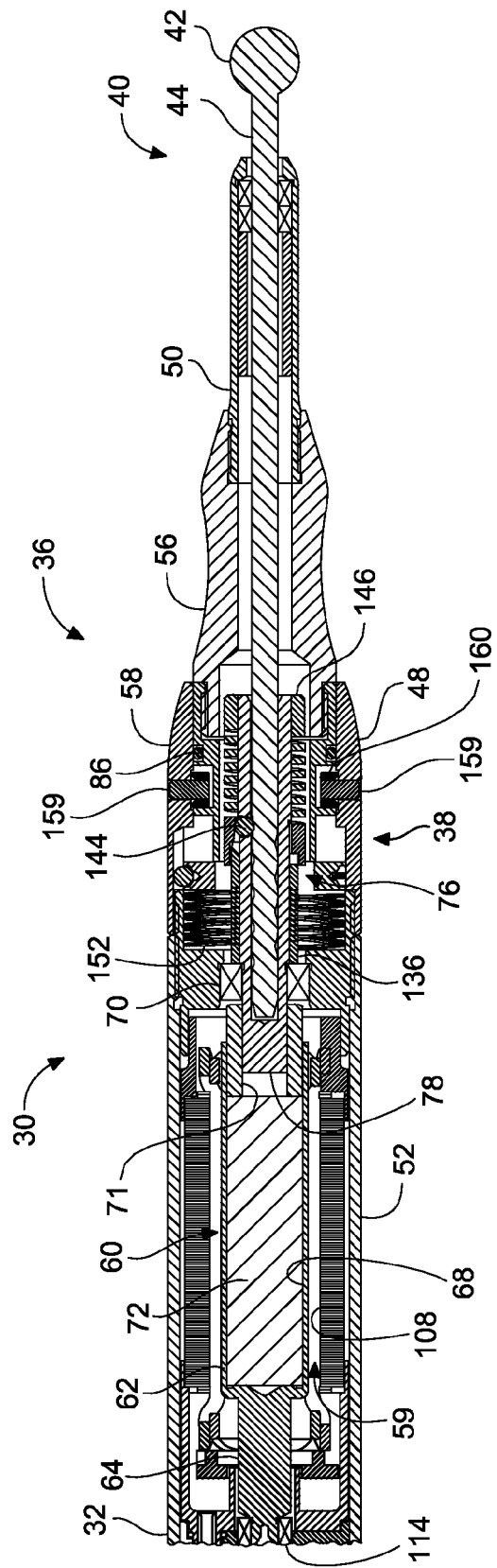
FIG. 2 is a cross-sectional view of the attachment of the tool system of this invention that contains the coupling assembly.

FIGS. 1 and 2 illustrate the basic components of the surgical tool system 30 of this invention. The system 30 includes a handpiece 32 in which a motor 34 (shown in phantom) is housed. An attachment 36 is rotatably and removably fitted to the front, distal end of the handpiece 32. The handpiece 32 includes tube-shaped shell 52 that forms the outer housing of the handpiece. A collar 58 extends forward from the distal end of shell 52. A coupling assembly 38 is disposed inside the handpiece 32. The coupling assembly 38 releasably holds an accessory 40 to the rest of the system 30. The accessory 40 may be a cutting tool, a saw blade, drill bit, buring device, or other type of accessory, or may provide an attachment to another device (not shown). The coupling assembly 38 also transfers the rotational power developed by the handpiece motor 34 to the accessory 40. Coupling assembly 40 also releaseably holds attachment 36 to handpiece 32.

The accessory 40 may include a head 42. The head 42 is the portion of the accessory 40 that is applied to the surgical site. A shaft 44 is formed integrally with the head 42 and extends rearwardly from the base of the head. The attachment coupling assembly 38 transfers the rotational power developed by the handpiece motor 34 to the accessory 40. Coupling assembly 38 and shaft 44 are also collectively designed so that the extent to which the shaft extends forward of the coupling assembly is selectively set through either coarse or fine adjustment (see below). This selectively allows the surgeon to regulate the extent to which the cutting accessory head 42 extends forward of the handpiece 32.

Throughout this application, it should now be understood that "forward", "front" and "distal" shall mean in a direction towards the head 42 of an accessory 40. "Rearward", "rear" and "proximal" shall mean in a direction towards the end of the handpiece 32 furthest from the accessory head 42.

A detailed understanding of the structure of the attachment 36 is obtained by initial reference to FIGS. 2 and 3. The attachment 36 includes a front end 50 and a base section 56. The front end 50 has an elongated tube shape so as to define an axially extending bore 49. Located rearwardly of the front end 50 is the base section 56. Base section 56 is wider in diameter than front end 50 and has an axially extending through bore 57. In many versions of the invention, front end 50 is threadedly secured into a counterbore at the distal end of base section bore 57 (counterbore not identified). Attachment 36 is rotated to move the coupling assembly 38 between the run state in which the coupling assembly holds the cutting accessory 40 for rotation and the load state in which the accessory 40 can be removed from or installed to the handpiece 32. Also, when the coupling assembly 38 is in the load state, the longitudinal position of the accessory 40 relative the handpiece 32 can be selectively set through either a course or fine adjustment (see below).

As best seen in FIGS. 2, 5, and 6, handpiece shell 52 is in generally in the form of a tube that is open at the opposed proximal and distal ends. At the proximal end, shell 52 has a threaded counterbore 53 (threading not shown). At the distal end, shell 52 is formed to have a threaded counterbore 55 (threading not illustrated). Both counterbores 53 and 55 have diameters slightly greater than diameter of the void space through the shell. A rotor 60, part of motor 34, is rotatably fitted in void space internal to handpiece shell 52. The rotor 60, seen best in FIG. 8, has a cylindrically shaped main section 62. A stem 64 extends rearwardly from main section 62. Stem 64 has an outer diameter less than that of main section 62. An axially extending closed-end bore 68 extends from the front end of rotor main section 60. The axially extending bore 68 holds a pie drive magnet assembly discussed below. From FIGS. 6 and 8 it can be seen that rotor 60 is coupled to an output drive shaft 76. The output drive shaft 76 is securely fitted to the rotor 60 by a sleeve-shaped front rotor end piece 71. The output drive shaft 76 is formed out of a single piece of metal that is shaped to have a cylindrical, solid stem section 78. The stem section 78 of the output drive shaft 76 is press fit into a bore of the front rotor end piece 71. Rotor end piece 71 is, in turn, press fit into the bore 68 of the rotor 60. This coupling arrangement ensures that rotor 60 and output drive shaft 76 rotate in unison.

Figure 15A:
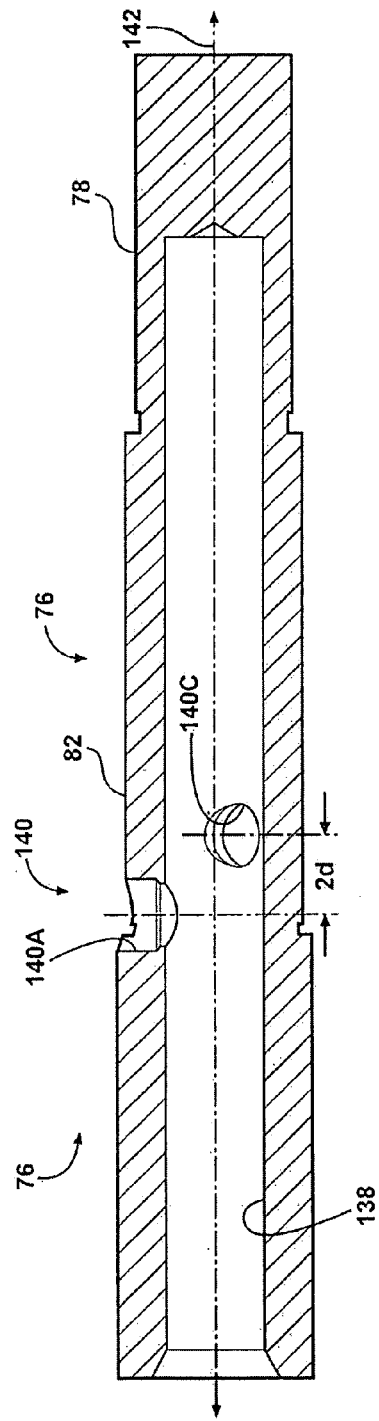
FIG. 15A is a side cross-section view of a drive shaft of the tool system of FIG. 1.
Figure 15B:
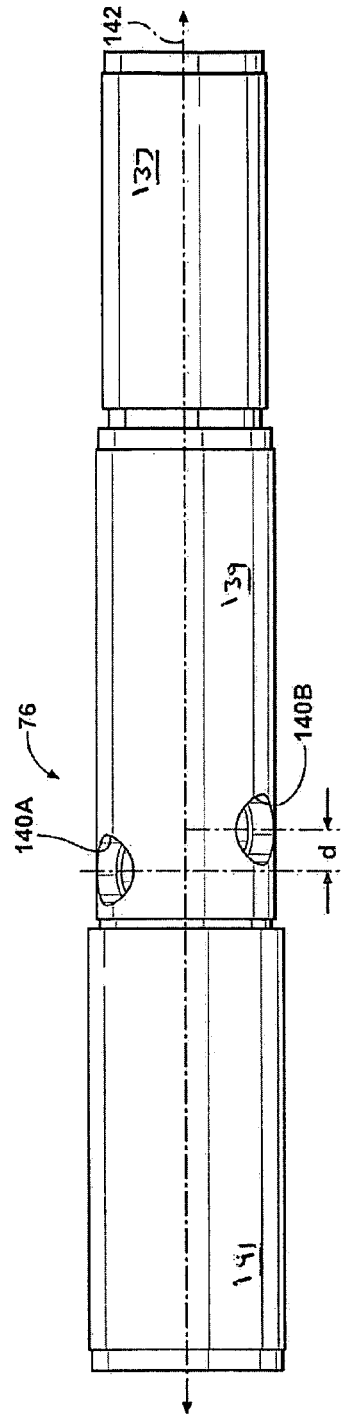
FIG. 15B is a side view of the drive shaft of FIG. 15A.

Output drive shaft 76 is further formed to have a main section 82, best seen in FIGS. 15A and 15B, which is located forward of stem section 78. The stem section 78 and the main section 82 are formed to have circular cross-sectional profiles. Further, it should be understood that the outer diameter of output drive shaft 76 is not constant along the length of the shaft. Around the stem 78 and the adjacent portion of the main section 82, shaft 76 has an outer circular wall 137. Forward of wall 137, around approximately the middle of the main section, shaft 76 has an outer circular wall 139. Wall 139 has a diameter greater than wall 137. Outer circular wall 141 is the most forward outer circular wall of the output drive shaft. Wall 139 has a diameter greater than the diameter of wall 137. Shown in FIG. 15B but relevant for manufacturing reasons only are the press fit steps at the opposed ends of the shaft 76, and adjacent the proximal end of wall 139, the undercut between walls 137 and 139 and the undercut between walls 139 and 141.

A bearing assembly 70 extends between the outside of output drive shaft section 62 and an adjacent inner circumferential wall of a front bearing housing 80. The front bearing assembly 80 is generally a tubularly shaped member that is disposed in and extends forward from the open distal end of handpiece shell 52. The bearing assembly 70 rotatably holds the front end of rotor 60 in handpiece shell 52. The rotor stem section 64 is rotatably held to a circular receiving plate 110 also disposed in the handpiece shell.

Output drive shaft 76 is formed with an axially extending, closed end bore 74 that extends rearward from the front end of stem section 78 to the front of the shaft. The bore 74 is the space internal to the coupling assembly 38 in which the proximal, rear end of the cutting accessory shaft 44 is fitted.

Figure 3B:
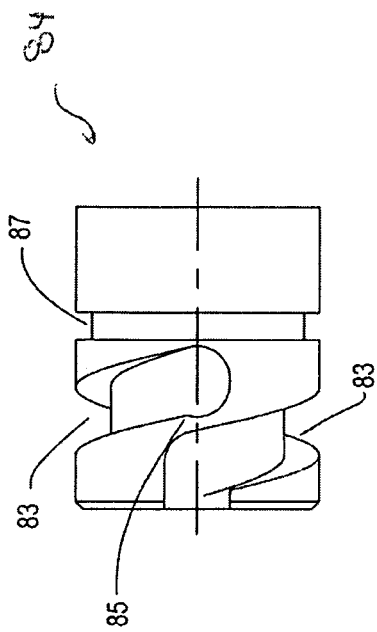
FIG. 3B is a plan view of the lock actuator
Figure 3A:
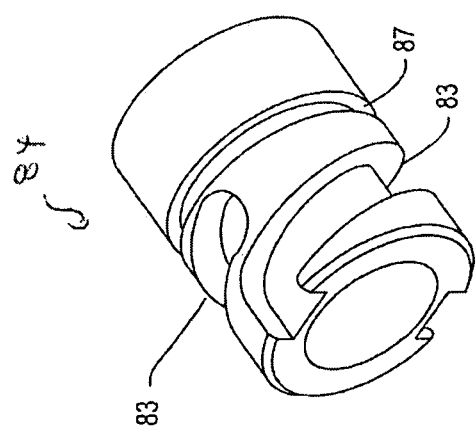
FIG. 3A is a perspective view of the lock actuator integral with the attachment.

Returning to FIGS. 3 and 4, it can be seen that attachment 36 further includes a lock actuator 84, an O-ring 86, a bearing retainer 88 and a duplex bearing pair 90. Lock actuator 84, now described by reference to FIGS. 3A and 3B, is generally in the form of a ring and extends proximally rearward from base section 56. In one version of the invention, lock actuator 84 is threadedly secured over the proximal end of base section 56. The lock actuator 84 is formed so as to have on the outer surface a pair of symmetrically opposed grooves 83. Each groove 83 extends in helical pattern upwardly from the proximal end of the lock actuator 84. Each groove 83 is further formed to at the distal closed end of the groove have a downwardly extending section so as to define a detent 85 in the lock actuator 84.

Lock actuator 84 is further formed to have a third groove, groove 87, in the outer surface. Groove 87 extends circumferentially around the outer surface of the lock actuator 84 forward of grooves 83.

Attachment front end 50 receives the cutting accessory 50. The attachment front end 50 has a nose 87 that is the most forward end of the front end. Nose 87 defines an opening into the front end bore 49 that has a diameter slightly greater than that of accessory shaft 44 and less than that of bore 49. Duplex bearing pair 90 is disposed in the bore front end bore 49 so that the outer race of the most forward bearing rests against the internal annular surface of the nose 87 that defines the nose opening. The duplex bearing pair 90 provides a rotating fit between accessory shaft 44 and accessory 36. The bearing retainer 88 is a generally C-shaped member that, prior to assembly of attachment 36, has an outer diameter larger than the diameter of the front end bore 49. The seating of the bearing retainer 88 in the front end bore compression holds the retainer 88 in the front end 88. When fitted in front end 50, bearing retainer abuts the proximal most of the bearings form pair 90 to hold the bearings of pair 90 in position.

The O-ring 86 is disposed in lock actuator groove 87. The attachment lock 84 works with the collar 58 (and other components) to lock the accessory 40 in place.

With particular reference to FIGS. 6, 11, and 12, the handpiece 32 includes a cable assembly 92. The cable assembly 92 includes a rear cap 94 which forms the end of the handpiece 32. Cable assembly 92 provides power to the motor 34 through a conductor cable 96. The cable assembly 92 also includes a compression ring 98 and a collet 100. Rear cap 92 is disposed over the proximal end opening of handpiece shell 52. The rear cap 94 includes an aperture 104 which allows the conductor cable 96 to be received in the handpiece 32. Collet 100 includes a tube-like skirt 101 that has an outer diameter that allows the base to be closely slip fitted inside handpiece shell 52. Flexible fingers 106 extend proximally rearward from the rear end of the collet skirt 101. Fingers 101 taper inwardly and are radially spaced apart from each other. Compression ring 98 has an outer cylindrical surface provided with threading (not illustrated). The compression ring 98 also has an axially extending through bore 97. The ring 98 is formed so that the through bore 97 does not have a constant diameter. Instead, compression ring 98 is formed so that bore 97 is tapered, the diameter of the bore 97 is smaller at the proximal end of the ring than at the distal end. Further, the diameter of bore 97, along the length of the bore is slightly less than the diameter of collet finger 101 along the length of the fingers.

When handpiece 32 is assembled, the distal end of cable 96 is feed through cap aperture 104, ring bore 97 between collet fingers 101 and extended forward of collet skirt 101. The conductors internal to the cable 96 are attached to the windings 108 (FIG. 17A) of motor 34. The above sub-assembly is disposed in handpiece shell 52. Compression ring 98 is screw secured in shell counterbore 53. The rotation of the compression ring 98 causes the inner surface of the ring that defines bore 97 to press against the collet fingers 106 and to squeeze the fingers inwardly. As result of the inward movement of collet fingers 106, the fingers compression hold cable 96 in position.

When the compression ring 98 is so secured to the handpiece shell 52, the proximal end of the ring extends rearwardly out of the proximal end of the shell. Rear cap 94 is screw secured over the exposed threading outer surface of the compression ring 98

When handpiece 32 is assembled, the distal end of cable 96 is feed through cap aperture 104, ring bore 97 between collet fingers 101 and extended forward of collet skirt 101. The conductors internal to the cable 96 are attached to the windings 108 (FIG. 17A) of motor 34. The above sub-assembly is disposed in handpiece shell 52. Compression ring 98 is screw secured in shell counterbore 53. The rotation of the compression ring 98 causes the inner surface of the ring that defines bore 97 to press against the collet fingers 106 and to squeeze the fingers inwardly. As result of the inward movement of collet fingers 106, the fingers compression hold cable 96 in position.

When the compression ring 98 is so secured to the handpiece shell 52, the proximal end of the ring extends rearwardly out of the proximal end of the shell. Rear cap 94 is screw secured over the exposed threading outer surface of the compression ring 98.

Disposed inside collet skirt 101 is a flex circuit. In FIG. 3, the flex circuit 113 is shown in the assembled folded state. Flex circuit 113 carries components used to control actuation of the motor 34 that are not relevant to this invention. One of these components is shown diagrammatically as a rectangular block 113a in FIG. 4. In some versions of the invention, after handpiece 32 is partially assembled, a potting compound (not illustrated) is flowed into collet skirt 101 to encapsulate the flex circuit 113.

Figure 13:
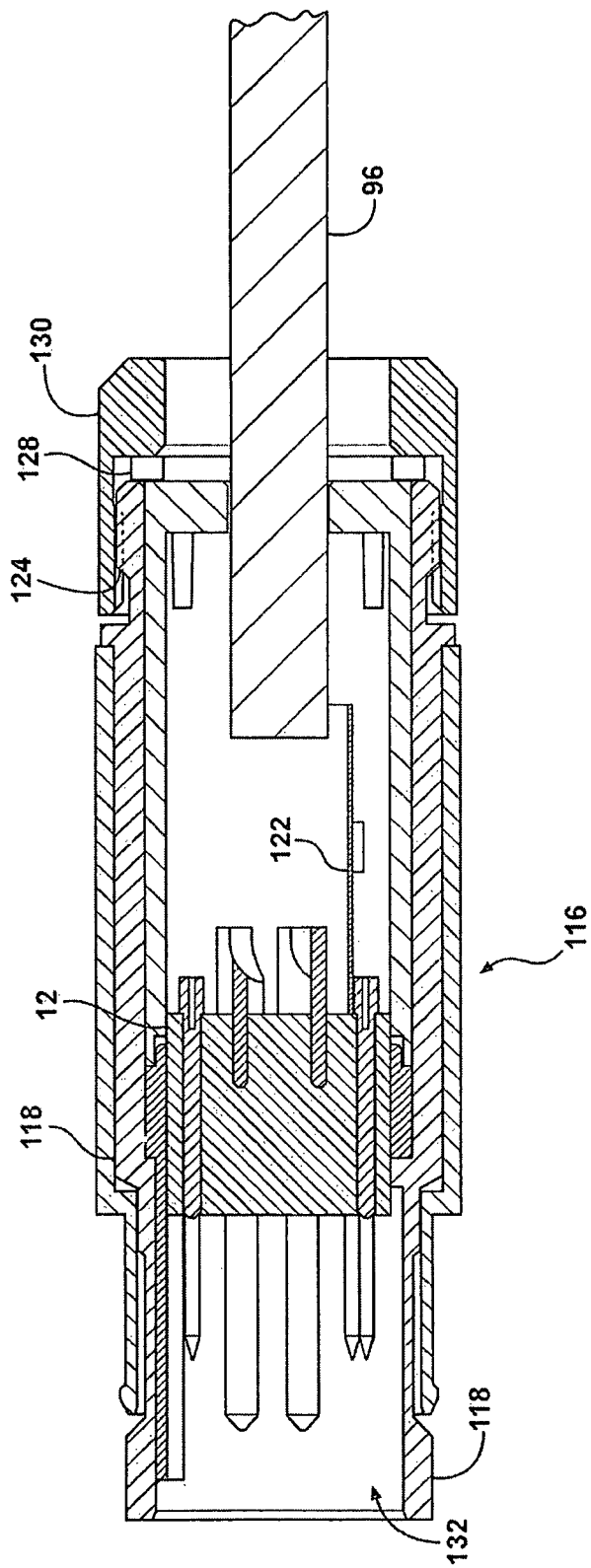
FIG. 13 is a cross-section view of a second portion of the cable assembly of FIG. 11.

With particular reference to FIGS. 11 and 13, the proximal end of cable 96 is coupled to an male connector assembly 116. The male connector assembly 116 is plugged into a suitable console or power source (not shown) for providing power to the handpiece 32. One such assembly is disclosed in the Applicant's Assignee's U.S. Pat. Pub. No. US 2007/0250098, MOTORIZED SURGICAL HANDPIECE AND CONTROLLER FOR REGULATING THE HANDPIECE MOTOR BASED ON THE INDUCTIVELY SENSED DETERMINATION OF MOTOR ROTOR POSITION, the contents of which is incorporated herein by reference. In the illustrated embodiment, the male connector assembly 116 includes cable main body 118, a male contact block 120, a flex circuit 122, a console bushing 124, a ground strap 126, a washer 128, and a retainer nut 130. The retainer nut 130 and bushing 120 receive an end of conductor cable. The component wires of the conduct cable 96 are electrically coupled to pins 132 of the male contact block 120 via the flex circuit 122. The component pieces of the male connecter assembly 116 snap together.

Coupling assembly 38 is described in greater detail. Specifically, as seen best in FIGS. 8 and 8C, it is noted that bearing housing 80 is shaped to have a cylindrical head 81. The outer surface of head 81 is formed with threading (not illustrated). Bearing housing 80 is shaped so that head 81 can be screw secured into housing shell counterbore 55. The components forming handpiece 32 are further shaped so that when the bearing housing 80 is so secured in shell 52, a portion of the bearing housing head extends forward from the shell. Bearing housing is further formed to have a sleeve-shaped skirt 75 that extends rearwardly from head 81. Skirt 75 is dimensioned to have an outer diameter that allows the skirt to be closely slip fitted in the cylindrical void space that extends through the housing shell 52.

A number of coaxial bores extend through bearing housing head 81. A first bore, bore 145, extends forward from the proximal end of the bearing head 81. Bore 145 is thus contiguous with the circular void space within bearing housing skirt 145. Extending forward from bore 145 is a bore 147. Bore 147 has a diameter less than the diameter of bore 145. A third bore, bore 150, is located forward from bore 147 and formed a distal end opening into the bearing housing 80. Bore 150 has a diameter greater than that of bore 145.

By reference to FIGS. 8A and 8B is can be seen that collar 58 is formed to have a number of coaxial, constant diameter bores that extend end-to-end through the collar. A first bore, bore 59 extends rearwardly from the distal end of the collar 58. A second bore, bore 61, extends from the proximal end of bore 59. Bore 61 has a diameter greater than bore 59. A third bore, bore 63, extends from the proximal end of bore 61 to form the proximal end opening into collar 58. Bore 63 has a diameter greater than the diameter of bore 61. While not illustrated, the inner annular wall of collar 58 that defines bore 63 is provided with threading. While not identified, the undercut present for manufacturing purposes between bores 61 and 63 is illustrated.

Collar 58 is further formed to have a groove 65. Groove 65 extends longitudinally along the inner annular wall of the collar 58 that defines bore 61. A pair of opposed diametrically opposed through holes 162 extend through the collar into bore 59. Internal to the collar 58 there are a pair of recesses 163 in the annular wall that defines bore 59. Each recess 163 extends around a separate one of the holes 162.

When handpiece 32 is assembled, the proximal end of the collar 58 that defines bore 63 is screw secured over the portion of the bearing housing head 81 that extends forward from shell 52.

FIGS. 9 and 10 provide a more detailed views of the motor rotor 60 and components of the coupling assembly 38. One or more washers 134 sit between the rotor end piece 71 and the bearings 70. The opposite side of the inner race of bearing 70 fits against a step in the output drive shaft 76 between outer circular wall 137 and outer circular wall 139. The forward edge of the outer race of bearing 70 rests against the step in bearing housing 80 between bores 145 and 147.

A ratchet spring 136 is disposed over the outer cylindrical wall 139 of the output drive shaft 76. The ratchet spring 136 is formed from a single piece of metal such as 465 Stainless Steel. As seen by reference to FIGS. 10A and 10B, the lock spring includes a ring shaped base 182 and a ring shaped head 186 spaced forward from the head. A helical spring element 184 extends between the base 182 and the head 186. More particularly, the spring element is formed to be flexible so the head 186 can be compressed towards the base 182. Ratchet spring 136 is further formed so that base 182 has an inner diameter that allows the base 182 to be press fit secured around that shaft outer cylindrical wall 139. The lock spring spring element 184 and head 186 have a common inner diameter that is larger than the inner diameter of the base 182. The larger inner diameter of spring element 184 and head 186 allow these components to move longitudinally over the shaft outer cylindrical wall 139.

Ratchet spring 136 is further formed so that the annular distally directed face of the head 186 is not a planar structure. Instead, the head is formed so that the face has three equangularly arcuately shaped steps 188, 190 and 192. Step 188 is the most forward of the steps. Step 190 is located rearward of step 188 and step 192 is located rearward of step 190. Collectively steps 188-192 form a circle, with in one direction of rotation: step 190 following step 188; step 192 following step 190; and step 188 following step 192.

The ratchet spring 136 is also shaped so there are three identically-shaped notches 194 extend inwardly from the inner circular wall of head 186. Each notch 194 extends proximally rearward from the top surface of a separate one of the steps 188, 190 and 192. Thus, the notches 194 are both angularly and longitudinally spaced apart from each other. Each notch 194 is centered relative to the step 188, 190 or 192 with which the notch is associated. Each notch 194 is shaped so that a cross-sectional slice taken of the notch along a plane perpendicular to the longitudinal axis of the spring 136 has a curved profile. However, the notches 194 are not of constant width or depth. As each notch 194 extends proximally from the top of the associated step 188, 190 or 192, both the depth and width of the notch decreases. None of the notches 194, even the notch associated with step 192, extend the whole length of spring head 186.

Returning to FIGS. 15A and 15B, it can be seen that the output drive shaft 76 has an interior bore 138 in the main section 82. The main section 82 also includes a plurality of apertures 140. In one aspect of the invention, the main section 82 includes an odd number of apertures 140. Apertures 140 extend through shaft outer circumferential wall 141. In the illustrated embodiment, the main section 82 includes first, second and third apertures, 140A, 140B, 140C. As shown, the apertures 140 are axially spaced, equally about an axis 142 of the output drive shaft 76. For example, the 3 apertures 140 in the illustrated embodiment are axially spaced 120° apart. Additionally, the apertures 140 are spaced longitudinally along the axis 142. In the illustrated embodiment, no two apertures 140 are in the same plane perpendicular to the axis 142. In one embodiment, the apertures 140 are longitudinally spaced along the axis a predefined distance, D. This distance D, is the same distance that separates the top of ratchet spring head edge step 188 from step 190 and that separates step 190 from step 192

Figure 15C:
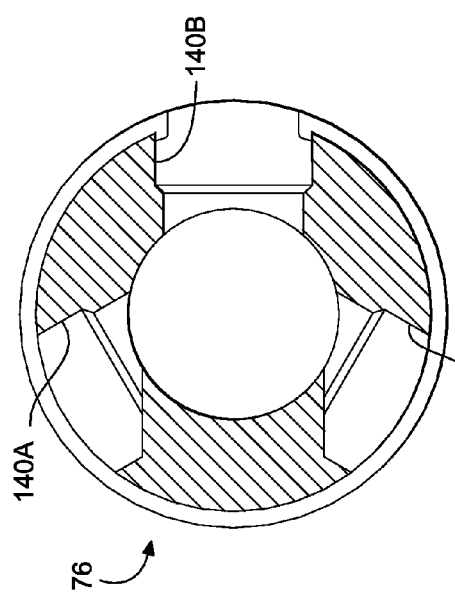
FIG. 15C is a second cross-section view of the drive shaft of FIG. 15A.

As best seen in FIG. 15C with respect to aperture 140B, each aperture 140 is in the form of a multi section co-axial bore (individual sections not identified). A first section with a first diameter extends inwardly from the shaft outer circumferential wall 139. At the base of the first section there is a second transition section with a diameter that tapers inwardly. A third section of constant diameter extends from the second section into shaft bore 138. The third section has a diameter smaller than the first section. In FIG. 15C it appears that the tapered and smallest diameter sections of apertures 140A and 140C are off axis with respect to the largest diameter sections. This is because 15C is a cross sectional view along the center longitudinal axis of aperture 140B. Owing to apertures 140A and 140C being longitudinally offset from each other and aperture 140B, in FIG. 15C the concentricity of the bore sections forming aperture 140A and the concentricity of the bore sections forming aperture 140C are not apparent.

Returning to FIGS. 8 through 10, fitted within the apertures 140 are locking elements, shown in the illustrated embodiment as ceramic balls 144. Each ball 144 has a diameter that allows the ball to project through the associated aperture 140 into the shaft bore 138 but not totally pass through the aperture so as to fall into the bore 138. (In FIGS. 6, 8 and 10, a single ball 144 is shown in only one of the holes.)

A tubular lock spring 146 is disposed over shaft outer circumferential wall 141 and the adjacent distal end of shaft outer circumferential wall 139. The lock spring, like ratchet spring 136 is formed as a single-piece unit and is formed from the same material from which the ratchet spring is formed. Lock spring 146, now described in detail with reference to FIGS. 14A, 14B and 14C, has a distal end ring shaped head 202 and a proximal end ring shaped foot 206. A helically shaped spring element 204, between head 202 and the foot 206 allows the head and foot to flex relative to each other. Spring head 202 has an inner diameter that allows the head to be press fit over the shaft outer circumferential wall 141 adjacent the distal end of the shaft 76. Lock spring spring element 204 and foot 206 have a common inner diameter that is greater than the inner diameter of shaft outer circumferential wall 141. This relative dimensioning of the output drive shaft 76 and lock spring 146 allows the spring spring element 204 and foot to move longitudinally over the shaft 76

Lock spring foot 206 is further formed so that the head 186 of the ratchet spring 136 can seat within the open end of the foot. The lock spring foot 206 is further formed so as to have to have two arcuately shaped steps 208 and 210 that are located forward the proximally directed end of the foot and that extend inwardly from the inner circumferential wall of the foot. Each step 208 and 210 subtends an arc of 120°. Step 208 is located a first distance distally forward of the proximal end of foot 206. Step 210 is located a second distance forward of the proximal end of the foot 206, the second distance being more than the first distance. When handpiece 32 is in assembled, the distal most portion of ratchet spring head, the portion that defines step 188, is seated in the void space below lock spring step 210. The portion of the ratchet spring 136 that defines step 190 is seated in the void space below lock spring step 208. The portion of the ratchet spring that defines step 192 is seated within the space immediately forward of the most proximal surface of the lock spring foot 206.

The lock spring foot 206 is also shaped so as to define three equangularly spaced apart notches 214. The notches 214 extend inwardly from the inner circumferential surface of the foot 206. A first one of the notches extends distally forward from the proximally directed bottom end of the foot 206. A second one of the notches 214 extends distally forward from step 208. The third notch 214 extends distally forward from step 210. Notches 214 are of identical shape. Each notch 214 has in the plane perpendicular to the longitudinal axis of the lock spring 146 are curved profile. Distal from where the notch 214 originates, the open end of the notch, the width and depth of the notch decreases. Notches 214 are further formed to receive the portions of balls 144 that project beyond the output drive shaft 76. Further the notches starting from the bottom end of the spring foot 206 and step 208 do not extend forward beyond the foot. The notch starting from step 210 extends forward from the distal end of the foot 206 a slight distance into the most proximal turn of spring element 204.

Also integral with lock spring foot 206 are two arcuately shaped symmetrically aligned keys 216. Keys 216 extend proximally rearward from the bottom end of the foot 206.

When handpiece 32 is assembled, the ratchet spring 136 has sufficient length so that if the spring 136 was able to completely expand, spring head 186 would be disposed over output drive shaft apertures 140. Similarly, lock spring 146, has sufficient length so that, in the expanded state, spring foot 206 extends over the output drive shaft apertures 206. The spring force of the lock spring 146 is greater than that of the ratchet spring 136. Accordingly, absent any other member being present, when springs 136 and 146 abut, the lock spring 146 outputs sufficient force to push the ratchet spring head 186 proximally away from the apertures 140.

Figure 7:
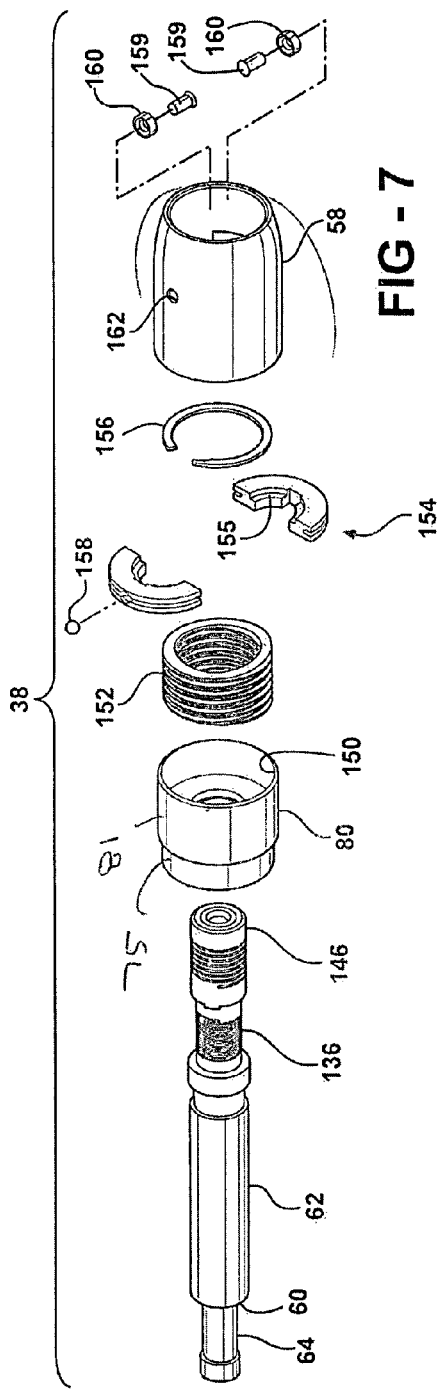
FIG. 7 is an exploded view of the coupling assembly of the handpiece.
Figure 7A:
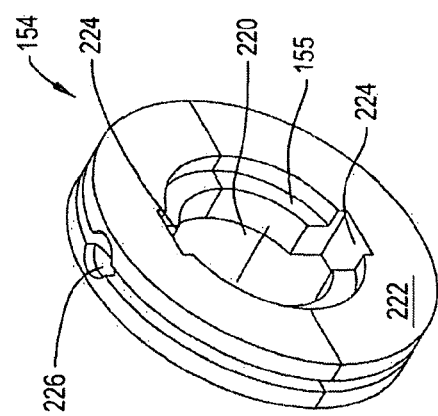
FIG. 7A is a perspective view of the lock release ring.

Coupling assembly 38 also includes a lock release ring 154, seen best in FIGS. 7 and 7A. The lock release ring 154 is formed out of two semicircular sections that are held together by a snap ring 156. The lock release ring 154 has a center opening 220 that allows the ring to be slidably fit over ratchet spring 136. When the two halves are assembled together, lock release ring 154 has a main body 222. Ring main body 222 has an outer diameter that allows the ring 154 to slide in bore 61 internal to collar 58. Snap ring 156 seats in a groove (not identified) that extends inwardly from the outer cylindrical face of ring main body 222. Inwardly of the main body 222, the lock release ring 154 has step 155 that is recessed inwardly of the distally directed face of the main body 222. Above step 155 the lock ring defines an annular void space, (space not identified). This annular void space has sufficient diameter to allow the proximal end of the lock spring foot 206 to seat in the space.

The lock release ring 154 is also formed so that in step 155 there are two diametrically opposed slots 224. Slots 224 also extend a slight distance into the inner perimeter of the ring main body 222. Each slot 224 is dimensioned to receive a separate one of the keys 216 integral with the lock spring foot 206.

The outer cylindrical surface of the lock release ring main body 222 is formed with a closed end bore 226. Bore 226 is shaped to partially receive a spherical bearing 158 seen in FIGS. 7 and 8. The portion of the bearing 158 that extends beyond ring 154 seats in groove 65 internal to collar 58. The engagement of bearing 158 with both collar 58 and the lock release ring 154 thus allows the ring to move longitudinally within the collar bore 65 while preventing rotation of the ring.

A wave spring 152, also part of coupling assembly 38, is disposed over ratchet spring 136. The wave spring 152 has a diameter that allows the spring to fit in the bore 150 internal to bearing housing 80. The proximal end of the wave spring 152 is seated against the distally facing surface of the bearing housing 50 that defines the base of bore 150. The distal end of the wave spring 152 seats against the proximally-directed face of the lock release ring 154.

When handpiece 32 of this invention is assembled, the lock release spring 146 and wave spring 152 act on opposed faces of the lock release ring 154. The components are selected so that wave spring 154 exerts a force greater than that exerted by the lock spring 146. Accordingly, when handpiece 32 is assembled, wave spring 152 pushes the lock release ring 154 and, by extension, lock spring 146 forward. The forward movement of these components is stopped by the abutment of the distally directed face of the lock release ring 154 against the annular step between collar bores 59 and 61.

Figure 8:
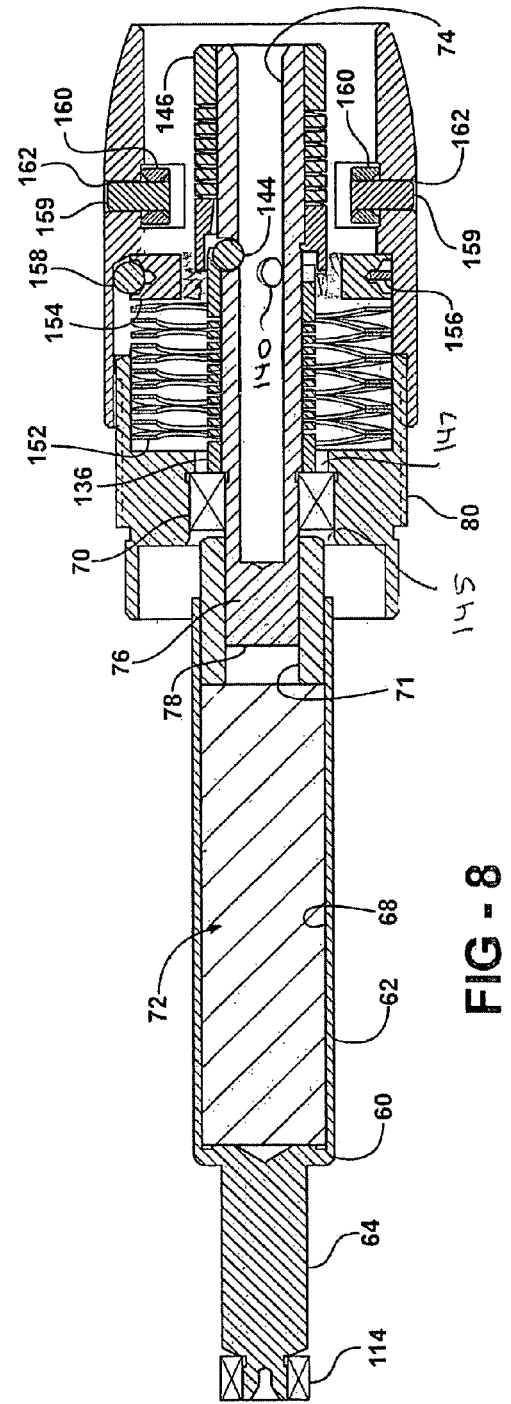
FIG. 8 is a cross-section of the coupling assembly of FIG. 7.
Figure 8C:
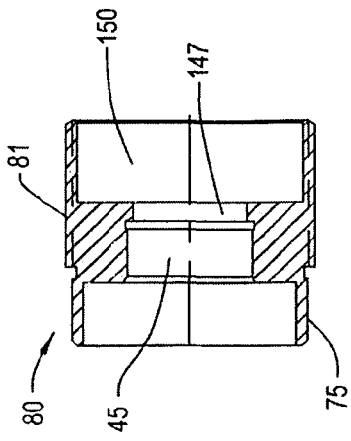
FIG. 8C is a cross sectional view of the handpiece bearing assembly.

Two diametrically opposed bushings 160, best seen in FIGS. 7 and 8, are rotatably mounted in collar bore 51. Each bushing 160 is rotatably mounted to a pin 159. The stem of each pin 159 is fitted into a separate one of the collar through holes 162. Each bushing 160 partially seats in and extends outwardly from the recess 163 internal to the collar 58 that surrounds each hole 162. Bushings 160 are dimensioned to travel in grooves 83 formed in the lock actuator 84.

Figure 17A:
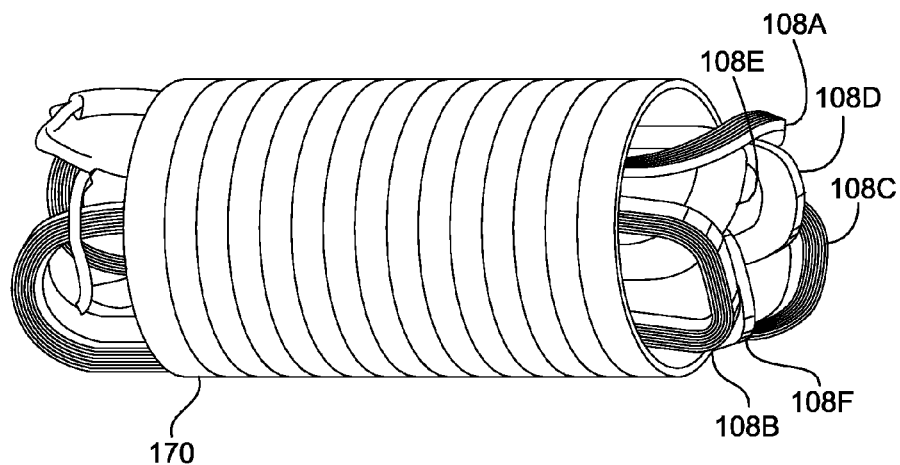
FIG. 17A is a view of a coil assembly according to one embodiment of the present invention.
Figure 17B:
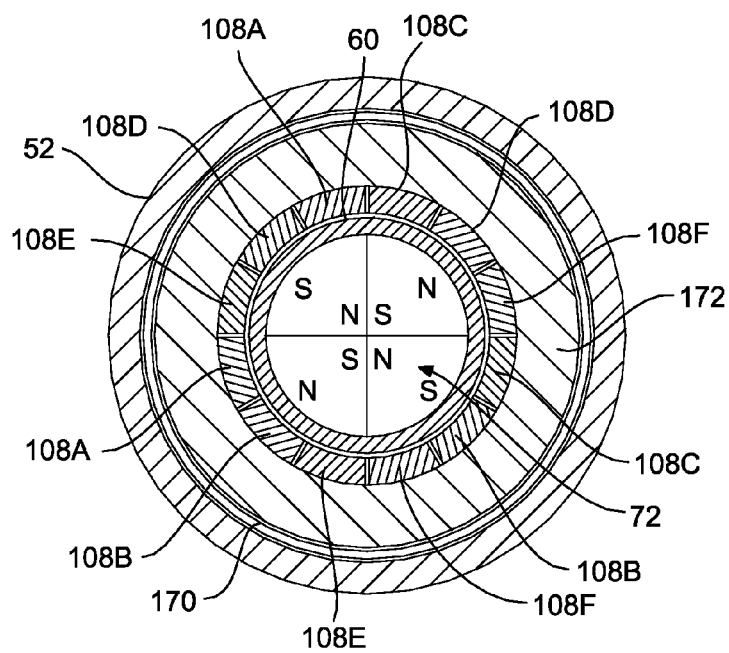
FIG. 17B is a cross-section of the motor of the tool system of FIG. 1.

The structure of the handpiece motor 34 is now discussed in more detail by initial reference to FIG. 17B. Motor 34 is a four-pole motor. Four magnets 72 are disposed in rotor bore 68. Each magnet 72 is generally in the shape of pie slice that subtends an arc of 90°. The North-South pole alignment of each magnet is such that one pole is located in corner where the two sides of the magnet meet and the opposed pole is located along the outer curved surface of the magnet. The magnets are collectively arranged so that two magnets with the North pole on their outer surfaces are diametrically aligned relative to each other. Accordingly, the magnets 72 with the South pole along their outer surfaces are similarly diametrically aligned.

Motor 34 also includes a lamination stack 170 and a set of windings 108. Lamination stack 170, now described by reference to FIGS. 6, 11 and 12, consists of a set of washer-shaped material formed from soft magnetizable material (individual washers not identified) that are stacked one on top of each other. The lamination stack 170 is disposed over the section of rotor 60 in which windings 108 are disposed. The lamination stack 170 is shaped so that, when disposed over the rotor 60, there is an annular void space between the rotor and the lamination stack.

Figure 12A:
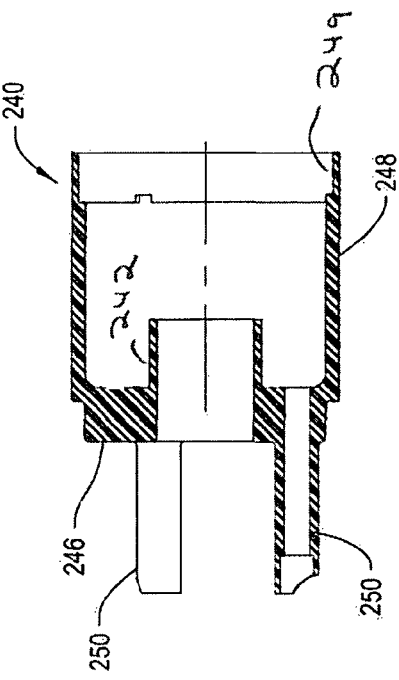
FIG. 12A is a cross sectional view of the lamination stack cap of FIG. 12.

The proximal end of the lamination stack is seated in a stack end cap 240, seen best in FIGS. 12 and 12A. Cap 240 is formed from plastic. Cap 240 consists of inner and outer coaxial sleeves 242 and 248, respectively. Inner sleeve 242 has a through bore, not identified, with a diameter greater than the diameter of rotor stem 64. At the proximal end of inner sleeve 242 a washer-shaped web 246 extends outwardly to connect the sleeves 242 and 248 together. Outer sleeve 248 extends over and is radially spaced away from inner sleeve 242. Outer sleeve 248 has a diameter that allows the sleeve 248 to be closely slip fit in handpiece shell 52. Outer sleeve 248 also extends forward from web 246 a distance greater than the distance inner sleeve 242 extends away from the web. Stack end cap 240 is further formed so as to have a counterbore 249 in the open end of outer sleeve 248.

Stack end cap 240 is further formed so that a number of rigid tubes 250 extend through web 246. In the described version of the invention there are three tubes 250 equangularly spaced around the longitudinal axis of the stack end cap 240. (Only two tubes 250 are seen in FIG. 12A.) Each tube 250 extends rearwardly away from the proximally directed end surface of the web 246. Tubes 250 function as the conduits through which the conductors integral with cable 96 pass so the conductors can be connected to the motor windings 108.

When handpiece 32 is assembled, the proximal end of the cap web 246 is disposed against the distal facing surface of receiver plate 110. Cap tubes 250 extend through opening 251 in the receiver plate. In FIG. 12 only a single opening 251 is shown. Rotor stem 64 extends through the center void space of the inner sleeve 242. The proximal end of the lamination stack 170 is seated in a counterbore 249 of outer sleeve 248.

In FIG. 12 a ring shaped circuit board 243 is disposed around the distal end of cap inner sleeve 242. Circuit board 242 supports components used to regulate the actuation of handpiece motor 34.

The distal end of the lamination stack 170 is seated in a stack front cap 252. Stack front cap 252 is from a single piece of plastic and is open at both ends. Cap 252 is formed to have a base 254. Base 254 has an outer diameter that allows the stack front cap 252 to be closely slip fit in handpiece shell 52. Forward of base 254, cap 252 has a head 256. Head 256 has an outer diameter less than that of base 254. Two bores, bores 258 and 260 extend axially through cap 238. Bore 258 extends forward from the distal end of cap base 254 partially through the base. Bore 260 extends from the distal end of bore 260 through the distal portion of base 254 and the whole of cap head 256. Bore 260 has a diameter less than that of bore 258.

When handpiece 32 of this invention is assembled, stack front cap head 256 is disposed against the inner circular wall of bearing housing skirt 75. The distal end of the lamination stack 170 is seated in cap bore 258.

Figure 17C:
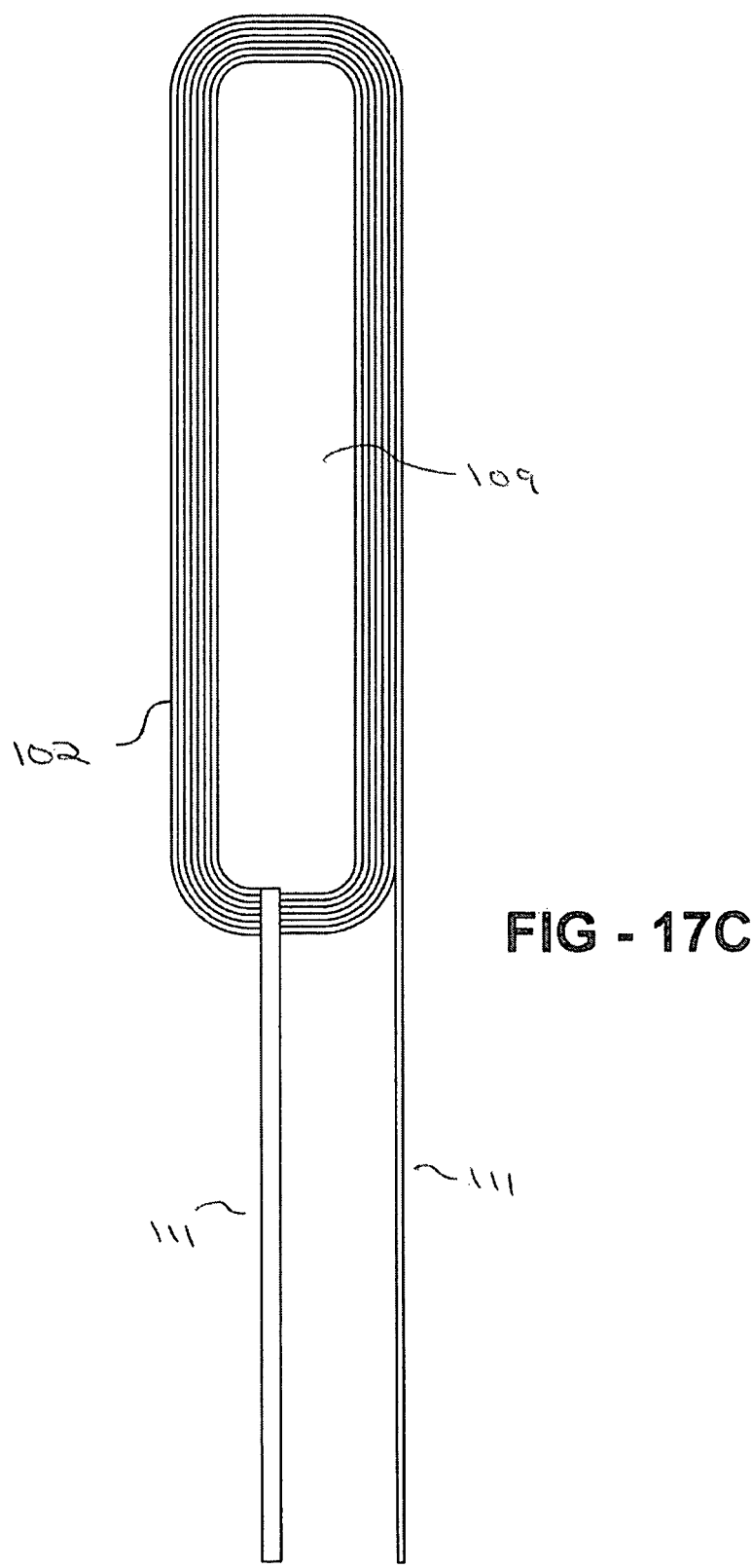
FIG. 17C is a first view of one of the windings of the coil assembly of FIG. 17A.

Windings 108 are disposed in the annular void space between the rotor 60 and the lamination stack 170. In the illustrated version of the invention, there are six windings 108A through 108F. FIG. 17C is representative of a single winding 108. The winding is formed out a wrap of wire 102. More particularly wire 102 is wire that has a rectangular cross sectional profile. In one version of the invention the wire 102 forming the windings 108 has a side-to-side width of between 0.13 and 0.38 mm and a top-to-bottom height of between 0.51 and 1.3 mm. The wire 102 is wrapped so that each winding 108 is generally in the form of a rectangular frame with rounded corners. Each winding 108 consists of multiple overlapping turns of the wire 102. The wire is looped so that the wide surfaced top and bottom surfaces of the wire abut. As seen in FIG. 17C owing to the structure of the windings 108, each winding defines a center located elongated void space 109. The opposed ends of each section of wire forming a winding 108 are the winding leads 111.

While not illustrated it should be appreciated that an insulating coating is disposed over the wires 102 forming the windings 108.

By reference to FIGS. 17A and 17B it can be seen that when handpiece 32 is assembled, the windings 108A-108F are placed against the inner annular surfaces of the washers that form lamination stack 170. The windings are arranged so as to be interleaved with each other. Thus, one elongated side of each of the windings 108D and 108E is disposed in the void space 109 between the elongated sides of winding 108A. Similarly, a first one of the elongated sides of winding 108A is disposed in the void space 109 between the sides of winding 108D. The second one of the elongated sides of winding 108A is disposed in the void space between the elongated sides of winding 108E.

When handpiece 32 is assembled, the opposed top and bottom ends of the windings extend out of, respectively, the distal and proximal ends of the lamination stack 170. Winding leads 111 extend out from the proximal rear end of the lamination stack. It is in these spaces in front of and behind the lamination stack that the windings 108 cross over each other so as to be interleaved. While not illustrated, it should be appreciated that the winding leads 111 are connected to the conductors integral with cable 96. It should also be appreciated that upon assembly of the handpiece 32, there is a small annular gap between the inner surfaces of the windings 108 and the rotor main section 62, the section of the rotor 60 in which magnets 72 are disposed.

The structure of a cutting accessory shaft 44 is now described by reference to FIGS. 16A-16D. Generally accessory shaft 44 has a cylindrical shape. Shaft is though further shaped to have, at the proximal end a tip 272 with a tapered shape. More specifically, the most proximal end of shaft tip 272, which is the most proximal end of the cutting accessory

40 is flat surfaced and has a diameter less than the diameter of the main body of the shaft 44. Tip 272 has an outer circumferential surface that is frusto-conical in shape and tapers outwardly to the diameter of shaft 44.

Located forward of tip 272, accessory shaft 44 is shaped to have a number of retention features 274. In the illustrated version of the invention, each retention feature 274 is in the form of an indentation in the shaft. Each retention feature 274 includes a center face 280 that is concave relative to the outer surface of the accessory shaft. Each center face 280 is curved around an axis that is perpendicular to the longitudinal axis of the shaft 44. The common radius of curvature of the retention feature center faces 280 is less than the radius of balls 144. Each retention feature 274 also includes a pair of opposed facets 278 that extend away from away from the opposed proximally and distally directed sides of the associated center face 280. Each facet 278 angles upwardly from the associated flat 274 to the outer surface of the accessory shaft. The length of each retention feature 274 between the ends of the opposed facets 278 is sufficient to accommodate at least a portion of the balls 144 in the void space between the facets.

Retention features 274 are arranged on the accessory shaft in plural angularly spaced apart columns. In the section of the "unwound" shaft shown in FIG. 16C, the shaft is shown to have 6 columns 280, 282, 284, 286, 288, 290 of retention features. There are plural retention features in each column 280-290 of retention features. In the illustrated version of the invention, the columns 280-290 of retention features are equangularly spaced apart from each other.

In the illustrated version of the invention, the retention features 274 in each column 280-290 of retention features are longitudinally spaced apart from each other. For example, in one version of the invention, each retention feature has a axial length "e" of approximately 2.1 mm and the spacing "f" between two adjacent, longitudinally aligned retention features is approximately 0.9 mm. Accordingly, the distance between the lateral axes of two adjacent longitudinally aligned retention features is 3.0 mm. These distances are understood to be exemplary, not limiting.

Cutting accessory 40 of this invention is further constructed so that the closest retention features in angularly adjacent columns are not laterally aligned with each other. Here, "laterally aligned" is understood to mean aligned along an axis perpendicular to the longitudinal axis of the shaft 44. Instead, the adjacent retention features 274 in angularly adjacent columns, for example in columns 284 and 286, are, at different distances relative to the proximal end of accessory shaft 244. The angular and longitudinal spacing of the retention features between adjacent columns gives the appearance that the retention features 274 are arranged in a helix around the shaft 44.

In the illustrated version of the invention, the retention features in one column are positioned so that their lateral axis are longitudinally offset from the lateral axis of the retention features in the angularly adjacent column by a distance equal to one-sixth the longitudinal distance separating adjacent retention features in a single column of retention features. Thus in FIG. 16C retention feature 274B in column 284 is spaced a distance of 0.50 mm above adjacent retention feature 274A in adjacent column 282. Also, retention feature 274B is spaced a distance of 0.5 mm below adjacent retention 274C in adjacent column 286.

Figure 16A:
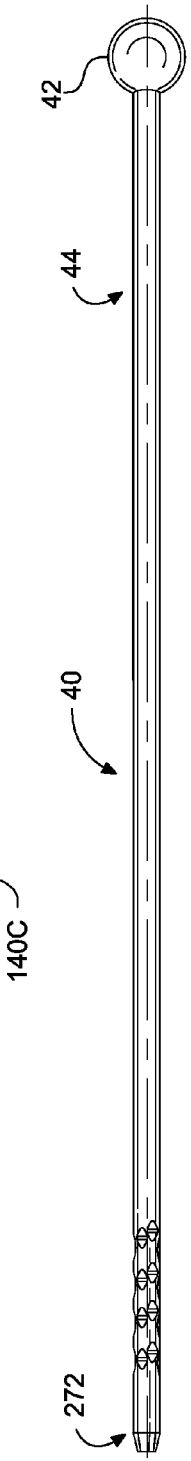
FIG. 16A is a side view of a cutting accessory of the tool system of FIG. 1.
Figure 16B:
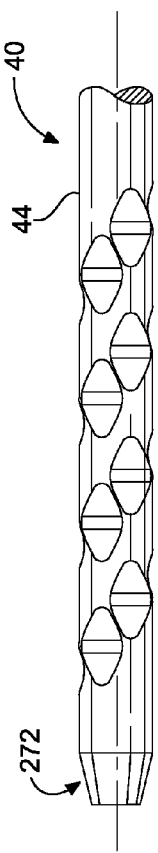
FIG. 16B is an enlarged view of an end of the cutting accessory of FIG. 16A.
Figure 16C:
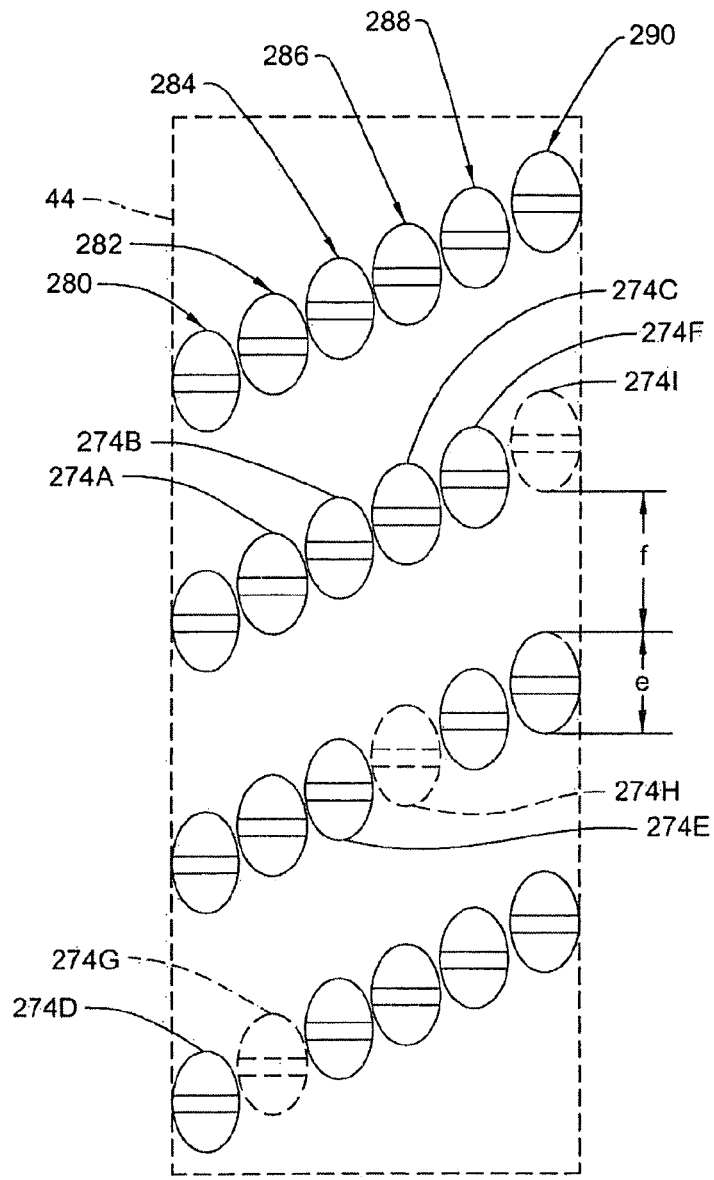
FIG. 16C is a planar view of the end of the cutting accessory of FIG. 16B.
Figure 16D:
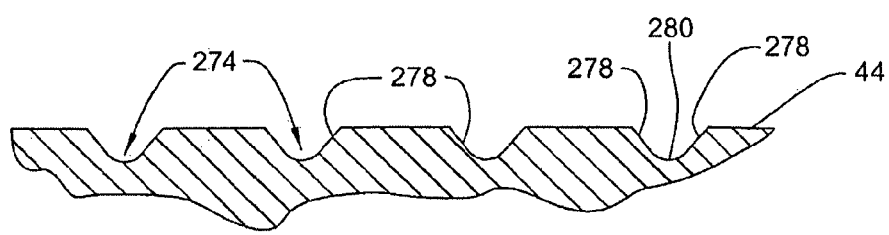
FIG. 16D is a cross-section of the end of the cutting accessory of FIG. 16C.

It can further be seen from FIG. 16C that the retention features 274 in adjacent columns of retentions features, for example the features of columns 284 and 286, subtend arcs around shaft 44 that partially overlap each other so that the two closest retention features in adjacent columns of retention features abut. This is also seen by the retention features 274 of FIG. 16B. Thus, there is a helix of abutting retention features around the shaft. It is further seen from both FIGS. 16B and 16C that the lateral axes of the two closest retention features in two adjacent columns of retention features are located different distances from the proximal end of shaft 44.

Initially, neither attachment 36 nor accessory 40 are attached to the handpiece 32 of this invention. When the handpiece 32 is in this state, wave spring 152 holds the lock release ring 154 in its full distally forward position, so the ring 154 abuts the annular step between collar bores 59 and 61 as seen in FIG. 8. Due to the lock release ring 154 being urged distally forward, the proximal end of the lock spring foot 206 abuts step 155 integral with the lock release ring. The spring force of the wave spring 152 is greater than that of the lock spring 146. Therefore, wave spring 152 not only holds the lock release ring 154 in the most forward position, the wave spring supplies enough force that the lock release ring 154 is able to hold the lock spring foot 206 away from apertures 140 in the drive shaft.

Since the lock spring foot 206 is held away from apertures 140, ratchet spring 136 is able to expand over the output drive shaft 76. Ratchet spring head 186 therefore extends around apertures 140. When spring head 186 is in this position, the exposed sections of each of the balls 144 located outwardly of the shaft 76 seat in separate ones of the notches 194 internal to spring head 186. More particularly, the ball 144 disposed in the most distal aperture, aperture 140A, seats in the notch 194 associated with the most distal step, step 188. Ball 144 in middle aperture 140B seats in the groove 194 associated with middle step 190. The ball associated with most proximal aperture 140C seats in the groove 194 of proximal step 192. As a result of spring head 186 surrounding the balls 144, the balls are subjected to a blocking force that prevent the balls from falling out of the apertures 140 and away from the output drive shaft 76. However, for reasons apparent below, ratchet spring 136 does not exert enough force to prevent the balls from being pushed out of shaft bore 138. When the coupling assembly 38 is in this state, the coupling assembly 38 is considered to be in the load state.

When coupling assembly 38 is in the load state, the lock release ring 154 does more than push lock spring foot 206 forward. As a consequence of the lock release ring 154 abutting lock spring foot 206, the keys 216 integral with the spring foot seat in the slots 224 internal to the lock release ring. As mentioned above, while the lock release ring 154 can move longitudinally relative to the other components of handpiece 32, the ring is blocked from rotation. Thus, when the handpiece is in the load state, the key-in-slot mating of the lock spring to the lock release ring prevents the spring and by extension the output drive shaft 76 from rotating. This component engagement prevents the inadvertent actuation of the output drive shaft and any accessory fitted to the shaft unless the coupling assembly is in the run state.

System 30 of this invention is prepared for use by first placing the front end attachment 36 over the handpiece 32. At this time though, attachment 36 is not fully inserted into the handpiece collar 80. Instead, the collar bushings 160 are threaded only partially through actuator grooves 83. At this time, while the proximal end of the attachment lock actuator 84 may abut the lock release ring, the lock actuator does not displace the lock release ring. Also at this time, attachment O-ring 86 extends into collar bore 59. The outer surface of the O-ring 86 abuts the adjacent annular wall of the collar 80 that defines bore 59 so as establish a manually releasable friction fit between the attachment 36 and the handpiece 32.

With the attachment 36 partially secured to the handpiece 32, the accessory 40 is then inserted. Accessory shaft 44 is inserted through the attachment so the proximal end tip 272 of the shaft enters the output drive shaft bore 138. Eventually the tapered surface of tip 272 abuts the portions of the balls 144 held in the bore by ratchet spring 136. Owing to its tapered profile, as shaft tip 272 is pushed inwardly the tip is able to overcome the force of the ratchet spring 136 and push the balls 144 outwardly.

As the shaft is moved proximally, each ball 144 moves in and out of the retention features 274 forming a separate one of the columns 280-292 of retention features. More particularly, the balls 144 seat in alternating columns of retention features. Thus, balls 144 seat in either the retentions features of columns 280, 284 and 288 or the retention features of columns 282, 286 and 290. As the shaft 44 is pushed into or retracted from shaft bore 138, the individual displacing the shaft overcomes varying amounts of force ratchet spring 136 imposes on the balls 144 as the balls move in and out of the retention features. The exposure to thee varying forces provides tactile feedback that the balls 144 are seating in different sets of retention features 274.

It should further be understood that, when a coupling assembly ball 144 seats in a shaft retention feature 274, the ball does not fully seat against the surfaces of the retention feature. That is, the ball abuts the opposed facets 278 of the retention. Thus, the individual ball-retention feature contact is along two opposing sections of a circle. This design feature allows for the manual force needed to overcome the force of the ratchet spring 136 to be established with some degree of precision.

During this process, there are two ways by which the length the cutting accessory 40 extends forward from the handpiece 32 can be selectively set. By pushing inwardly linearly or pulling outwardly linearly on the accessory 40, the each ball 144 seats sequentially in the retention features of a single one of the columns 280, 282, 284, 286, 288 or 290 of retention features. Each time the balls 144 move in and out a set of retention features, the shaft moves a distance equal to the distance between the centers of adjacent retention features in a single column of retention features. This adjustment of shaft extension/retraction is the coarse adjustment of accessory extension.

Alternatively, the accessory shaft 44 may be rotated helically. When the shaft 44 is so rotated, the balls alternative from seating in the retention features 274 integral with columns 280, 284 and 288 to the retention features integral with columns 282, 286 and 290. Again, the retention features in adjacent columns are longitudinally offset from each other by a distance of one-sixth the intra-column separation of adjacent retentions. Thus, each rotation of the shaft by 60° results in the extension or retraction of the shaft by a distance equal to one-sixth of the longitudinally aligned retention features that form a single column of retention features. For example, by helically rotating the shaft 44, the shaft can be displaced from a position in which balls 144 seat in retention features 27474D 274E and 274F (features shown in bold in FIG. 16C) associated with, respectively, columns 280, 284 and 288 to the position in which the balls set in retention features 274G, 274H and 274I. These later retention features 274G, 274H, 274I, (shown in phantom in FIG. 16C) are associated with, respectively, columns 282, 286 and 290. This adjustment of accessory shaft 44 extension/retraction is the fine adjustment of accessory extension.

Once the position of the accessory shaft 44 is set, coupling assembly 38 placed in the run state. This action is performed by helically rotating the attachment 36 so that the lock actuator 84 is urged proximally toward the handpiece motor 36. Attachment 80 is rotated until the coupling assembly bushings 160 seat in the distal ends of the lock actuator slots 83, beyond detents 85. As a consequence of the proximal displacement of the attachment 36, the bottom face of the lock actuator 83 abuts and pushes the lock release ring 154 proximally. In other words, the force the individual exerts in rotating the attachment 84 proximally is sufficient to overcome the force the wave spring 152 exerts on holding the lock release ring 154 in the distal position.

As a consequence of the rearward displacement of the lock release ring 154, lock spring 206 is free to expand. Lock spring spring element 204 pushes the spring foot 206 proximally. Since the lock spring spring element 204 has more spring force than ratchet spring spring element 184, lock spring foot 206 pushes ratchet spring head 186 away from the section of shaft 76 in which apertures 140 are formed. Lock spring foot 206 extends over apertures 140. More particularly, the lock spring 146 is fitted to the output drive shaft 76 so that when the spring foot 206 extends proximally rearwardly, each one of the balls 144 seats in one of the notches 214 formed in the foot. Specifically, the ball 140 seated in distal most shaft aperture 140A seats in the notch 214 associated with step 210. The ball 140 seated in middle aperture 140B seats in the notch 214 associated with step 208. The ball 144 seated in most proximal aperture 140C seats in the notch 214 that extends forward from the most proximal end of the spring foot 206.

Lock spring 146 is further constructed so that spring element 204 will withstand tangential forces cutting accessory shaft 44 imposes on coupling assembly balls 144. Thus, when the spring foot 206 is disposed over the coupling assembly balls 144 the coupling assembly can be considered in the run state in which the assembly holds the cutting accessory 40 so that the accessory moves in unison with the handpiece output drive shaft 76.

The displacement of the lock release ring 154 away from the lock spring foot 206 does more than allow the lock spring to lock the cutting accessory 40 to the handpiece output drive shaft 76. As a consequence of the rearward movement of lock release ring 154 away from lock spring foot 206, foot keys 216 are freed from lock ring slots 224. This disengagement of the lock spring 146 from the lock release ring 154 allows the spring 146, and, by extension, output drive shaft 76, to rotate freely when motor 34 is actuated.

When the coupling assembly 38 is in the run state, the lock release ring 154 continues to press against the lock actuator 84 so as to push attachment 36 forward. As a consequence of this displacement of the attachment 80, handpiece bushings 80 set in the end of lock actuator grooves 83, below the edges of the adjacent detents 85. This seating of the bushings 160 in the distal ends of grooves 83 releaseably secures the attachment 36 to the handpiece 32.

During actuation of system 30, attachment O-ring 86 serves a seal that prevents fluids to which the system is exposed from flowing between attachment 36 and handpiece collar 58.

Once the attachment 36 and cutting accessory 40 are locked to the handpiece 32, the practitioner can reset the extent to which the attachment shaft 44 extends forward from the handpiece. This adjustment is performed by pushing down and then rotating the attachment 36 so that the attachment moves forward away from the handpiece collar 58. Wave spring 152, through the lock release ring 154, pushes the attachment 36 forward. The friction imposed by O-ring 86 prevents the force output by wave spring 152 from pushing the attachment 36 completely out of the collar bore 59. Nevertheless, the lock release ring 154 is displaced forward a sufficient distance so that the ring 154 displaces the lock spring foot 206 away from the shaft apertures 140. Coupling assembly 38 is returned to the load state to allow the extension or retraction of the accessory shaft 44. Once the position of the accessory 44 is reset, the attachment 36 is rotated back down over the handpiece 32 to return the coupling assembly 38 to the run state.

It should be appreciated that the foregoing is directed to one specific version of the invention. Other versions of the invention may have features different from what has been described. For example, there is no requirement that all versions of the invention have the disclosed motor 34 or the disclosed coupling assembly.

Thus versions of the invention with alternative electric motors are possible. Likewise, it is possible to construct a version of this with a pneumatic or hydraulic motor.

Likewise, alternative versions of this invention with coupling assemblies different from what has been described in detail may be provided. For example in some versions of the invention, locking elements other than balls may be employed to hold the accessory shaft to the handpiece output drive shaft. Thus in some versions of this invention a collet with spring loaded feet may perform this function. In these versions of the invention, the collet feet extend into the output drive shaft bore to function as the locking elements. In these and other versions of the invention, the natural spring tendency of the collet feet to stay in the bore may eliminate the need to provide a ratchet spring to hold the feet (locking elements) in position.

Also, there is no requirement that in all versions of the invention three locking elements be present. Normally to prevent side loading of the accessory shaft 44, there are at least two equangularly spaced locking elements. However, some constructions of the coupling assembly may only require a single locking element. In other versions of the invention, four or more locking elements may be present.

Likewise, there is no requirement that in all versions of the invention the lock actuator that places the coupling assembly 38 in the load state be part of the removable attachment. In some embodiments of this invention, this lock actuator, which may not even be ring shaped, may be moveably fitted to the handpiece. When the practitioner wants to transition the coupling assembly between the load and run states a drive member, such as a button, on the handpiece is displaced. The displacement of the drive member, which is connected to the lock actuator, results in a similar displacement of the lock actuator to cause the desired load/run state transition of the coupling assembly.

It should be appreciated then that in some versions of the invention a spring may not be employment as the lock member that selectively retains the lock elements in the run position. In some versions of the invention a ring or sleeve that is manually displaced between the load and run positions performs this function.

In some versions of the above embodiment of the invention, the handpiece may not even be designed to receive an attachment. In alternative versions, a second coupling assembly is used to releaseably couple the attachment to the handpiece.

Likewise, it should be appreciated that the above-described coupling assembly that includes an attachment may even be included in an attachment. Thus in this embodiment of the invention the attachment has its own output drive shaft. The coupling assembly allows the above described coarse or fine adjustment of the extent the accessory shaft extends forward from the attachment.

Similarly, it should be appreciated that the accessory retention features and complementary coupling assembly locking elements may have geometries that vary from what has been described. In some versions of the invention, the accessory retention features may even be tabs or other members that extend outwardly from the surface of the accessory shaft 44. In some versions of the invention, the retention features may be V-shaped, W-shaped or partially spherical or circular-shaped indentions in the accessory shaft. In these versions of the invention, the handpiece coupling assembly locking elements are shaped to seat over or in these features.

Also, in some versions of the invention, the retention features in a single column of retention features may not be spaced apart from each other. Thus, along the shaft immediately proximal or distal to where one retention feature ends, another retention feature starts. Similarly, in the disclosed version of the invention, the retention features 274 is adjacent columns of retention features partially overlap. In some versions of the invention, there may be some radial separation between adjacent columns of retention features. In some versions of the invention, the retention features in adjacent columns of retention features may not longitudinally overlap with each other.

It should also be appreciated that in some versions of system 30 of this invention the ratio of handpiece coupling assembly locking elements to columns of shaft retention features may be different from the disclosed 1:2 ratio. In some versions of the invention, this ratio may be 1:1. Thus with regard to versions of the invention with three locking elements each 120° helical turn of the shaft would result in shaft length fine adjustment that is one-third a single coarse adjustment. Alternatively, the ratio can be greater than 1:2. For example in a system of this invention wherein the handpiece coupling assembly has two locking elements, the shaft may have eight retention features per 360° turn of the shaft. In this version of the invention, a 45° rotation of the shaft would result in fine adjustment of the shaft extension or retraction that is one-eighth a single coarse adjustment.

Likewise, the actual tissue working member at the distal end of the cutting accessory shaft 44 may be different from described and illustrated bur head.

Therefore, it is an object of the appended claims to cover all such variations and modifications that come within the true spirit and scope of this invention.

What is claimed is:

1. A cutting accessory for use with a powered surgical handpiece, said accessory including:
   an elongated shaft having opposed proximal and distal ends and a longitudinal axis that extends between the ends;
   a tissue working member attached to the distal end of said shaft; and
   a plurality of retention features formed in said shaft distal to the proximal end, each said retention feature being configured to engage with a coupling member integral with the power surgical tool to which said cutting accessory is attached so that the engagement of the coupling member with the retention feature holds said shaft to the tool and said retention features being arranged in columns that extend longitudinally along said shaft, each column including a plurality of longitudinally aligned retention features, the columns of retention features being angularly spaced from each other around said shaft, and each retention feature having a lateral axis that is perpendicular to the longitudinal axis of said shaft wherein:

in each column of retention features the lateral axes of adjacent retention features are longitudinally spaced apart a common distance along said shaft, the common distance being the same for each column of retention features; and the angularly adjacent columns of retention features are longitudinally spaced along said shaft so that the lateral axes of two said retention features in angularly adjacent columns of retention features that are closest to each other on said shaft are longitudinally offset from each other along said shaft and are longitudinally offset from each other a distance less than the common distance between the lateral axes of the longitudinally adjacent retention features that are in the same column of retention features.

2. The cutting accessory of claim 1, wherein each said retention feature is an indentation in said shaft.

3. The cutting accessory of claim 1, wherein, in each column of retention features, the longitudinally adjacent retention features are longitudinally spaced apart from each other.

4. The cutting accessory of claim 1, wherein, at the proximal end of said shaft, there is a tip, said tip shaped so that, extending distally along said tip, said tip tapers outwardly.

5. The cutting accessory of claim 1, wherein the tissue working member is a bur or a drill bit.

6. The cutting accessory of claim 1, wherein, in each column of retention features, the longitudinally adjacent retention features are not longitudinally spaced apart from each other.

7. The cutting accessory of claim 1, wherein the retention features are formed so that the two closest retention features in the angularly adjacent columns of retention features partially overlap.

8. The cutting accessory of claim 1, wherein said shaft is formed to have six columns of retention features.

9. The cutting accessory of claim 8, wherein the retention features are further formed on said shaft so that the lateral axes of the two closest retention features in angularly adjacent columns of retention features are longitudinally spaced apart from each other a distance equal to one-sixth of the common distance between the lateral axes of the longitudinally adjacent retention features that are in the same column of retention features.

10. The cutting accessory of claim 1, wherein the retention features are further formed on said shaft so that the lateral axes of two adjacent retention features in angularly adjacent columns of retention features are longitudinally spaced apart from each other a distance equal to one-sixth of the distance between the lateral axes of the longitudinally adjacent retention features that are in the same column of retention features.

11. A cutting accessory for use with a powered surgical tool, said cutting accessory including:

a head for application to a surgical site;

a shaft that extends from said head, said shaft having a distal end adjacent said head, a proximal end opposite the distal end and a longitudinal axis that extends between the distal and proximal ends; and a plurality of retention features formed in said shaft, each said retention feature being configured to engage with a coupling member integral with the powered surgical tool to which said cutting accessory is attached so that the engagement of the coupling member with the retention feature holds said shaft to the tool and each said retention feature has a lateral axis that is perpendicular to the shaft longitudinal axis, wherein said retention features are arranged in plural columns wherein:

each column consists of a plurality of retention features that extend longitudinally along said shaft;

the columns are arranged so as to be angularly spaced around said shaft; and the columns are further arranged so that, longitudinally along said shaft the lateral axes of two closest adjacent retention features in two angularly adjacent columns are longitudinally spaced apart from each other along said shaft.

12. The cutting accessory of claim 11, wherein each said retention feature is an indentation in said shaft.

13. The cutting accessory of claim 11, wherein, in each column of retention features, the longitudinally adjacent retention features are longitudinally spaced apart from each other.

14. The cutting accessory of claim 11, wherein, at the proximal end of said shaft, there is a tip, said tip having shaped so that, extending distally along said tip, said tip tapers outwardly.

15. The cutting accessory of claim 11, wherein said head is a bur or a drill bit.

16. The cutting accessory of claim 11, wherein, in each column of retention features, the longitudinally adjacent retention features are not longitudinally spaced apart from each other.

17. The cutting accessory of claim 11, wherein said shaft is formed to have six columns of retention features.

18. The cutting accessory of claim 17, wherein the retention features are further formed on said shaft so that the lateral axes of two adjacent retention features in angularly adjacent columns of retention features are longitudinally spaced apart from each other a distance equal to one-sixth of the distance between the lateral axes of longitudinally adjacent retention features that are in the same column of retention features.

19. The cutting accessory of claim 11, wherein the retention features are further formed on said shaft so that the lateral axes of two adjacent retention features in angularly adjacent columns of retention features are longitudinally spaced apart from each other a distance equal to one-sixth of the distance between the lateral axes of longitudinally adjacent retention features that are in the same column of retention features.

20. A cutting accessory for use with a powered surgical tool, said cutting accessory including:

a head for application to a surgical site;

a shaft that extends from said head, said shaft having a distal end adjacent said head, a proximal end opposite the distal end and a longitudinal axis that extends between the distal and proximal ends; and a plurality of retention features formed in said shaft, each said retention feature being configured to engage with a coupling member integral with the powered surgical tool to which said cutting accessory is attached so that the engagement of the coupling member with the retention feature holds said shaft to the tool and each said retention feature has a lateral axis that is angularly offset from the shaft longitudinal axis, wherein said retention features are arranged in plural columns wherein:

each column consists of a plurality of retention features that extend longitudinally along said shaft wherein, along the column, the lateral axes of longitudinally adjacent retention features are spaced apart a common distance and the common distance is the same for each column of retention features;

each column is angularly spaced from the adjacent column around said shaft; and the columns of retention features are not laterally aligned with each other along said shaft so that the lateral axes of two closest adjacent retention features in angularly adjacent columns of retention features are at different distances from the proximal end of said shaft and so that, longitudinally along said shaft, the two adjacent retention features in the angularly adjacent columns at least partially overlap.

21. The cutting accessory of claim 11, wherein, in each column of retention features, the longitudinally adjacent retention features are longitudinally spaced apart from each other.

22. The cutting accessory of claim 1, wherein said retention features are arranged so that the two closest retention features in the two angularly adjacent columns of retention features abut so that the two closest retention features form a portion of a helix that extends around said shaft.

23. The cutting accessory of claim 11, wherein said retention features are arranged so that the two closest retention features in the two angularly adjacent columns of retention features abut so that the two closest retention features form a portion of a helix that extends around said shaft.

* * * * *